United States Patent
Volpe

(10) Patent No.: US 10,923,228 B2
(45) Date of Patent: *Feb. 16, 2021

(54) DOWNLOADING AND BOOTING METHOD AND SYSTEM FOR A WEARABLE MEDICAL DEVICE

(71) Applicant: ZOLL Medical Corporation, Chelmsford, MA (US)

(72) Inventor: Shane S Volpe, Saltsburg, PA (US)

(73) Assignee: ZOLL Medical Corporation, Chelmsford, MA (US)

( * ) Notice: Subject to any disclaimer, the term of this patent is extended or adjusted under 35 U.S.C. 154(b) by 28 days.

This patent is subject to a terminal disclaimer.

(21) Appl. No.: 16/275,363

(22) Filed: Feb. 14, 2019

(65) Prior Publication Data

US 2019/0180869 A1    Jun. 13, 2019

Related U.S. Application Data

(63) Continuation of application No. 15/053,635, filed on Feb. 25, 2016, now Pat. No. 10,269,452.
(Continued)

(51) Int. Cl.
*G16H 40/40* (2018.01)
*G06F 8/65* (2018.01)
(Continued)

(52) U.S. Cl.
CPC ........... *G16H 40/40* (2018.01); *A61N 1/0484* (2013.01); *A61N 1/3968* (2013.01);
(Continued)

(58) Field of Classification Search
CPC ............. G06F 19/3412; G06F 11/1417; G06F 9/4408; G06F 8/65; G06F 9/4401;
(Continued)

(56) References Cited

U.S. PATENT DOCUMENTS

| 4,928,690 A | 5/1990 | Heilman et al. |
| 5,078,134 A | 1/1992 | Heilman et al. |

(Continued)

FOREIGN PATENT DOCUMENTS

| KR | 101017379 | 2/2011 |
| WO | 20040027541 | 4/2004 |
| WO | 20120097356 | 7/2012 |

OTHER PUBLICATIONS

Supplementary European Search Report for Application No. 16756347, dated Sep. 26, 2018, 8 pages.

*Primary Examiner* — Rex R Holmes
(74) *Attorney, Agent, or Firm* — The Webb Law Firm

(57) ABSTRACT

A wearable medical monitoring device includes a plurality of ECG electrodes configured to receive an ECG signal when the wearable medical monitoring device is worn by a patient, and a monitor coupled to the plurality of ECG electrodes. The monitor is configured to detect an impending cardiac event based on the received ECG signal of the patient. The device includes at least one processor configured to execute a plurality of instructions to implement an update manager configured to receive a software update corresponding to the at least one software module for the monitor, determine an event estimation of risk score for a predetermined period of time, cause an installation of the update when the event estimation of risk score indicates a low likelihood of an impending cardiac event, and cause a delay in the installation when the event estimation of risk score indicates a high likelihood of impending cardiac event.

16 Claims, 9 Drawing Sheets

Related U.S. Application Data

(60) Provisional application No. 62/126,067, filed on Feb. 27, 2015.

(51) Int. Cl.
  *G06F 9/4401* (2018.01)
  *G06F 11/14* (2006.01)
  *A61N 1/39* (2006.01)
  *A61N 1/04* (2006.01)

(52) U.S. Cl.
  CPC .......... *A61N 1/3993* (2013.01); *G06F 8/65* (2013.01); *G06F 9/4401* (2013.01); *G06F 9/4408* (2013.01); *G06F 11/1417* (2013.01); *G06F 11/1433* (2013.01)

(58) Field of Classification Search
  CPC . G06F 11/1433; A61N 1/0484; A61N 1/3968; A61N 1/3993
  See application file for complete search history.

(56) References Cited

U.S. PATENT DOCUMENTS

| | | |
|---|---|---|
| 5,741,306 A | 4/1998 | Glegyak et al. |
| 5,944,669 A | 8/1999 | Kaib |
| 6,065,154 A | 5/2000 | Hulings et al. |
| 6,253,099 B1 | 6/2001 | Oskin et al. |
| 6,280,461 B1 | 8/2001 | Glegyak et al. |
| 6,681,003 B2 | 1/2004 | Linder et al. |
| 8,271,082 B2 | 9/2012 | Donnelly et al. |
| 8,369,944 B2 | 2/2013 | Macho et al. |
| 8,904,214 B2 | 12/2014 | Volpe et al. |
| 8,954,719 B2 | 2/2015 | Dicks et al. |
| 10,269,452 B2 * | 4/2019 | Volpe .................. A61N 1/3968 |
| 2003/0095648 A1 | 5/2003 | Kaib et al. |
| 2005/0022060 A1 | 1/2005 | Hashimoto et al. |
| 2009/0099866 A1 | 4/2009 | Newman |
| 2013/0231711 A1 | 9/2013 | Kaib |
| 2013/0283256 A1 | 10/2013 | Proud |
| 2015/0039039 A1 | 2/2015 | Macho et al. |
| 2015/0039042 A1 | 2/2015 | Amsler et al. |

\* cited by examiner

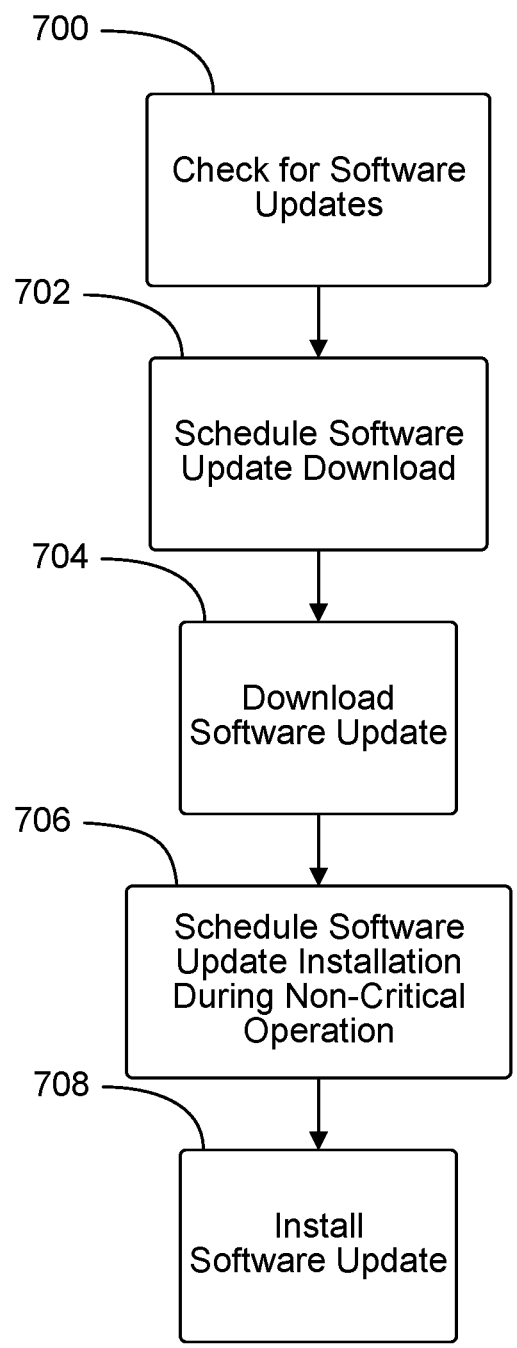

DOWNLOADING AND BOOTING METHOD AND SYSTEM FOR A WEARABLE MEDICAL DEVICE

CROSS REFERENCE TO RELATED APPLICATIONS

This application claims priority under 35 U.S.C. § 120 as a continuation of U.S. patent application Ser. No. 15/053,635 titled "Downloading And Booting Method And System For A Wearable Medical Device," filed Feb. 25, 2016, now U.S. Pat. No. 10,269,452, which claims priority under 35 U.S.C. 119(e) to U.S. Provisional Patent Application No. 62/126,067 titled, "Downloading And Booting Method And System For A Wearable Medical Device," filed Feb. 27, 2015, each of which are incorporated herein by reference in their entireties.

BACKGROUND

Technical Field

The present disclosure relates to a medical monitoring and/or treatment device and, in some aspects, to downloading and booting systems and methods for a medical monitoring and/or treatment device.

Description of Related Art

Technology is available for correcting excessively slow heart rates (bradycardia) using implantable devices, commonly referred to as pacemakers, which deliver microjoule electrical pulses to a slowly beating heart in order to speed the heart rate up to an acceptable level. Also, it is well known to deliver high energy shocks (e.g., 180 to 360 joules) via external paddles applied to the chest wall in order to correct excessively fast heart rates, and prevent the possible fatal outcome of ventricular fibrillation or certain ventricular tachycardias. Bradycardia, ventricular fibrillation, and ventricular tachycardia are all electrical malfunctions (arrhythmias) of the heart. Each can lead to death within minutes unless corrected by the appropriate electrical stimulation.

One of the deadliest forms of heart arrhythmias is ventricular fibrillation, which occurs when the normal, regular electrical impulses are replaced by irregular and rapid impulses, causing the heart muscle to stop normal contractions and to begin to quiver. Normal blood flow ceases, and organ damage or death can result in minutes if normal heart contractions are not restored. Although frequently not noticeable to the victim, ventricular fibrillation is often preceded by ventricular tachycardia, which is a regular but fast rhythm of the heart. Because the victim has no noticeable warning of the impending fibrillation, death often occurs before the necessary medical assistance can arrive.

Because time delays in applying the corrective electrical treatment can result in death, implantable pacemakers and defibrillators have significantly improved the ability to treat these otherwise life-threatening conditions. Being implanted within the patient, the device continuously monitors the patient's heart for treatable arrhythmias and, when such an arrhythmia is detected, the device applies corrective electrical pulses directly to the heart.

Normal heart function often can be restored to a person suffering ventricular fibrillation or ventricular tachycardia by a procedure known as cardioversion, the synchronized application of electrical therapy to the heart muscle. Pacemakers and defibrillators that apply corrective electrical pulses externally to the patient's chest wall also are used to correct such life-threatening arrhythmias, but suffer from a drawback insofar as it cannot be possible to apply the device in time during an acute arrhythmic emergency to save the patient's life. Such treatment is needed within a few minutes to be effective.

Consequently, when a patient is deemed at high risk of death from such arrhythmias, electrical devices often are implanted so as to be readily available when treatment is needed. However, patients that have recently had a heart attack or are awaiting such an implantable device, can be kept in a hospital where corrective electrical therapy is generally close at hand. Long-term hospitalization is frequently impractical due to its high cost, or due to the need for patients to engage in normal daily activities.

External wearable defibrillators have been developed for patients that have recently experienced a heart attack, that are susceptible to heart arrhythmias and are at temporary risk of sudden death, and that are awaiting an implantable device. While these wearable defibrillators have been widely accepted and have a good reputation in the marketplace, it remains desirable to develop improvements of such devices.

SUMMARY

In one example, a wearable medical monitoring device can comprise: a monitor configured to monitor a physiological parameter of a subject, the monitor comprising at least one processor configured to execute a plurality of instructions according to at least one software module; and an update manager configured to receive a software update corresponding to the at least one software module for the monitor and cause an installation of the software update such that the at least one software module is updated. A time period to install the software update can be determined based on an operational state of the wearable medical monitoring device.

The time period to install the update can be further determined based upon an operational state of the remote server. Alternatively, the time period to install the software update can be specified at a remote server from which the software update is made available. In another example, the time period to install the software update is determined based on the physiological parameter of the subject.

The monitor can be configured to calculate, for the time period, an event estimation of risk score associated with a potential medical event for the subject occurring within the time period based on the physiological parameter of the subject. In this example, the monitor can be configured to determine the time period to install the software update based on the event estimation of risk score.

In an example, the monitor can comprise a processor including a first core and a second core. The first core of the processor can be configured to install the software update, and the second core of the processor can be configured to monitor the physiological parameter of the subject independent of the first core and simultaneous to installation of the software update by the first core.

In another example, the wearable medical monitoring device can comprise a medical treatment device configured to deliver a medical treatment to the subject. The medical treatment can comprise an electric shock. The monitor can be configured to delay installation of the software update when the medical treatment device is delivering the medical treatment to the subject.

In an example, the monitor and a remote server from which the software update is made available can be configured to determine if the software update is for a critical function of the monitor. The one of the monitor and the remote server can be configured to delay the time period for installation of the software update based on the determination that the software update affects the critical function. The one of the monitor and the remote server can be configured to delay the software update, cancel indefinitely the software update, or only partially carry out the software update based on the determination that the software update affects a critical function of the monitor.

In one example, the time period to install the software update can be determined based on whether the software update affects a function for at least one of delivering a therapeutic pulse, charging one or more capacitors, providing an alert to the patient, addressing a patient-related event detected by the device, addressing a device-related event detected by the device, and deploying conductive gel on the patient's skin. In another example, the time period to install the software update can be determined based on whether the software update affects a function for one or more of determining, preparing, and applying a treatment to the subject. In yet another example, the time period to install the software update can be determined based on whether the software update affects a function for one or more of determining, preparing, and notifying the subject and/or another party of a current or future medical event for the subject. In still another example, the time period to install the software update can be determined based on whether the software update affects a function that is scheduled for use during the time period to install the software update. In an example, the time period to install the software update can be determined based on one or more of the following: a time needed for download, unpacking, and installation of the software update; a size of the software update; and a relationship of a type of the software update to a function of the device currently in use or scheduled for future use.

In another example, the monitor can be configured to automatically install the software update in response to a maintenance operation performed on the wearable medical monitoring device, the wearable medical monitoring device being assigned to a new subject, or an instruction from an authorized user. The monitor can be configured to provide a prompt to the subject or an authorized user to install the software update. The monitor can be configured to install the software update when the subject is not wearing the wearable medical monitoring device. The monitor can be configured to access a plurality of different media drives, and the monitor can be configured to install the software update to a first media drive and maintain boot availability and operation of the wearable medical monitoring device based on a second media drive during the installation to the first media drive.

In an example, the monitor can be configured to determine a download period to download the software update based on a data usage of a cellular data modem and a data usage threshold. The monitor can be configured to determine a projected data usage for the download period based on a history of data usage during one or more previous download periods and a schedule of future data downloads.

In an example, a method of downloading a software update to a wearable medical monitoring device can comprise: receiving a software update for the wearable medical monitoring device; determining a time period for installing the software update based on a use of the wearable medical monitoring device; determining if the software update is for a critical function of the wearable medical monitoring device; and delaying the time period for installation of the software update based on the determination that the software update affects the critical function.

In another example, a wearable medical monitoring device can comprise: at least one processor; and a supervisory circuit configured to monitor a state of the at least one processor when the at least one processor is configured to boot from a current drive, and wherein the supervisory circuit is configured to control the at least one processor to boot from an alternative drive different from the current drive based on the state of the at least one processor.

The supervisory circuit can be configured to monitor a number of times that the at least one processor enters a failure state when configured to boot from the current drive. The supervisory circuit can be configured to control the at least one processor to boot from the alternative drive if the number satisfies a threshold number.

In one example, the supervisory circuit can be configured to control the at least one processor to reboot from the current drive if the number does not satisfy the threshold. The failure state can include a failure of the at least one processor to boot from the current drive. In another example, the failure state can include a failure of an application executing on the at least one processor after booting from the current drive. The supervisory circuit can be configured to determine that the at least one processor has entered the failure state based on a lack of communication from the at least one processor for a predetermined time period. The supervisory circuit can be configured to monitor a communication state of the at least one processor. The supervisory circuit can be implemented on a programmable logic device.

In one example, if the supervisory circuit detects a boot error or an operating error for the at least one processor, the supervisory circuit can be configured to control the at least one processor to attempt to reboot from the current drive a predetermined number of times, and, after the supervisory circuit controls the at least one processor to reboot from the current drive a predetermined number of times, the supervisory circuit can be configured to control the at least one processor to boot from the alternative drive.

In another example, a wearable medical monitoring device can comprise: at least one processor; and a supervisory circuit configured to control the at least one processor to reboot from a current drive a predetermined number of times in response to a boot error or an operating error of the at least one processor. After the supervisory circuit controls the at least one processor to reboot from the current drive the predetermined number of times, the supervisory circuit can be configured to control the at least one processor to boot from an alternative drive different from the current drive.

In one example, a wearable medical monitoring device can comprise: a monitor configured to monitor a physiological parameter of a subject, the monitor including a processor including a plurality of boot selection pins for setting a boot order of the processor; and circuitry configured to control one or more of the boot selection pins based on a control signal from a supervisory circuit. The boot order can indicate an order in which the processor checks a plurality of ports for a drive including executable code.

In an example the circuitry can comprise a programmable logic device (PLD), an application-specific integrated circuit (ASIC) device, and a field-programmable gate array (FPGA) device.

In one example, the supervisory circuit can be implemented in the circuitry and comprises a watchdog timer. The circuitry can comprise a counter. The counter can be configured to increment a count based on an expiration of the watchdog timer. The circuitry can be configured to control the one or more boot selection pins based on the count of the counter. In an example, the circuitry can be configured to send a reboot command to the processor based on an expiration of the watchdog timer. The expiration of the watchdog timer can be based on a communication state of the circuitry with a software application of the monitor. The circuitry can activate the one or more boot selection pins when the count satisfies a count threshold. The circuitry can control the one or more boot selection pins to have a default value when the count does not satisfy the count threshold, and the monitor can be configured to check a first port in the order of the plurality of ports indicated by the boot order when the one or more boot selection pins have the default value. The monitor can be configured to check a next port after the first port in the order of the plurality of ports indicated by the boot order when the circuitry activates the one or more boot selection pins.

In one example, for a corresponding checked port of the plurality of ports, the circuitry can be configured to determine that the executable code on the drive is corrupted or a physical error exists in the drive. The monitor can be configured to automatically notify a remote server that the code on the drive is corrupted or the physical error exists in the drive. The monitor can be configured to copy a code image from a drive associated with a next port of the plurality of ports indicated by the boot order onto a drive associated with a port of the plurality of ports associated with the drive that is determined to be corrupted or have a physical error. If executable code exists on a drive associated with a current port checked by the processor, the processor can be configured to execute the code. If no executable code exists on a drive associated with a current port checked by the processor, the processor can be configured to check a next port of the plurality of ports in the boot order for a drive including executable code. The circuitry can be configured to provide an interface between the processor and at least one other processor. The one or more boot selection pins can be hardwired directly to the circuitry.

In one example, the wearable medical monitoring device can further comprise a medical treatment device configured to deliver a medical treatment to the subject.

In another example, a method of booting a wearable medical monitoring device can comprise: monitoring a state of at least one processor of the wearable medical monitoring device with a supervisory circuit when the at least one processor is configured to boot from a current drive; and controlling, with the supervisory circuit, the at least one processor to boot from an alternative drive different from the current drive based on the state of the at least one processor.

In an example, a wearable medical monitoring device comprises a monitor configured to monitor a physiological parameter of a subject, wherein the monitor is configured to communicate with a distribution node including a processor connected to a plurality of electrodes, and wherein the monitor is configured to determine if the distribution node is compatible with the monitor. In another example, the monitor can be configured to determine if a hardware version and/or software version of the distribution node is compatible with the monitor. In one example, the monitor is configured to determine a time period to update the software version of the distribution node based on a use of the distribution node.

Preferred and non-limiting embodiments or aspects of the present disclosure will now be described in the following numbered clauses:

Clause 1. A wearable medical monitoring device, comprising: a monitor configured to monitor a physiological parameter of a subject, the monitor comprising at least one processor configured to execute a plurality of instructions according to at least one software module; and an update manager operably connected to the monitor and configured to receive a software update corresponding to the at least one software module for the monitor, and cause an installation of the software update such that the at least one software module is updated, wherein a time period to install the software update is determined based on an operational state of the wearable medical monitoring device.

Clause 2. The wearable medical monitoring device of clause 1, wherein the time period to install the software update is further determined based on an operational state of the remote server.

Clause 3. The wearable medical monitoring device of clause 1 or 2, wherein the time period to install the software update is specified at a remote server from which the software update is made available.

Clause 4. The wearable medical monitoring device of any of clauses 1-3, wherein the time period to install the software update is determined based on the physiological parameter of the subject.

Clause 5. The wearable medical monitoring device of clause 4, wherein the monitor is configured to calculate, for the time period, an event estimation of risk score associated with a potential medical event for the subject occurring within the time period based on the physiological parameter of the subject, and wherein the monitor is configured to determine the time period to install the software update based on the event estimation of risk score.

Clause 6. The wearable medical monitoring device of any of clauses 1-5, wherein the monitor comprises: a processor including a first core and a second core, wherein the first core of the processor is configured to install the software update, and wherein the second core of the processor is configured to monitor the physiological parameter of the subject independent of the first core and substantially simultaneous to installation of the software update by the first core.

Clause 7. The wearable medical monitoring device of any of clauses 1-6, further comprising: a medical treatment device configured to deliver a medical treatment to the subject.

Clause 8. The wearable medical monitoring device of clause 7, wherein the medical treatment comprises an electric shock.

Clause 9. The wearable medical monitoring device of clauses 7 or 8, wherein the monitor is configured to delay installation of the software update when the medical treatment device is delivering the medical treatment to the subject.

Clause 10. The wearable medical monitoring device of any of clauses 1-9, wherein one of the monitor and a remote server from which the software update is made available is configured to determine if the software update is for a critical function of the monitor, and wherein the one of the monitor and the remote server is configured to delay the time period for installation of the software update based on the determination that the software update affects the critical function.

Clause 11. The wearable medical monitoring device of any of clauses 1-10, wherein the one of the monitor and the remote server is configured to delay the software update, cancel indefinitely the software update, or only partially carry out the software update based on the determination that the software update a critical function of the monitor.

Clause 12. The wearable medical monitoring device of any of clauses 1-11, wherein the time period to install the software update is determined based on whether the software update affects a function for at least one of delivering a therapeutic pulse, charging one or more capacitors, providing an alert to the patient, addressing a patient-related event detected by the device, addressing a device-related event detected by the device, and deploying conductive gel on the patient's skin.

Clause 13. The wearable medical monitoring device of any of clauses 1-12, wherein the time period to install the software update is determined based on whether the software update affects a function for one or more of determining, preparing, and applying a treatment to the subject.

Clause 14. The wearable medical monitoring device of any of clauses 1-13, wherein the time period to install the software update is determined based on whether the software update affects a function for one or more of determining, preparing, and notifying the subject and/or another party of a current or future medical event for the subject.

Clause 15. The wearable medical monitoring device of any of clauses 1-14, wherein the time period to install the software update is determined based on whether the software update affects a function that is scheduled for use during the time period to install the software update.

Clause 16. The wearable medical monitoring device of any of clauses 1-15, wherein the time period to install the software update is determined based one or more of the following: a time needed for download, unpacking, and installation of the software update, a size of the software update, and a relationship of a type of the software update to a function of the device currently in use or scheduled for future use.

Clause 17. The wearable medical monitoring device of any of clauses 1-16, wherein the monitor is configured to automatically install the software update in response to a maintenance operation performed on the wearable medical monitoring device, the wearable medical monitoring device being assigned to a new subject, or an instruction from an authorized user.

Clause 18. The wearable medical monitoring device of any of clauses 1-17, wherein the monitor is configured to provide a prompt to the subject or an authorized user to install the software update.

Clause 19. The wearable medical monitoring device of any of clauses 1-18, wherein the monitor is configured to install the software update when the subject is not wearing the wearable medical monitoring device.

Clause 20. The wearable medical device of any of clauses 1-19, wherein the monitor is configured to access a plurality of different media drives, and wherein the monitor is configured to install the software update to a first media drive and maintain boot availability and operation of the wearable medical monitoring device based on a second media drive during the installation to the first media drive.

Clause 21. The wearable medical monitoring device of any of clauses 1-20, wherein the monitor is configured to determine a download period to download the software update based on a data usage of a cellular data modem and a data usage threshold.

Clause 22. The wearable medical device of clause 21, wherein the monitor is configured to determine a projected data usage for the download period based on a history of data usage during one or more previous download periods and a schedule of future data downloads.

Clause 23. A method of downloading a software update to a wearable medical monitoring device, comprising: receiving a software update for the wearable medical monitoring device; determining a time period for installing the software update based on a use of the wearable medical monitoring device; determining if the software update is for a critical function of the wearable medical monitoring device, and delaying the time period for installation of the software update based on the determination that the software update affects the critical function.

Clause 24. A wearable medical monitoring device, comprising: at least one processor; and a supervisory circuit configured to monitor a state of the at least one processor when the at least one processor is configured to boot from a current drive, and wherein the supervisory circuit is configured to control the at least one processor to boot from an alternative drive different from the current drive based on the state of the at least one processor.

Clause 25. The wearable medical monitoring device of clause 24, wherein the supervisory circuit is configured to monitor a number of times that the at least one processor enters a failure state when configured to boot from the current drive, and wherein the supervisory circuit is configured to control the at least one processor to boot from the alternative drive if the number satisfies a threshold number.

Clause 26. The wearable medical device of clause 25, wherein the supervisory circuit is configured to control the at least one processor to reboot from the current drive if the number does not satisfy the threshold.

Clause 27. The wearable medical monitoring device of clauses 25 or 26, wherein the failure state includes a failure of the at least one processor to boot from the current drive.

Clause 28. The wearable medical monitoring device of any of clauses 25-27, wherein the failure state includes a failure of an application executing on the at least one processor after booting from the current drive.

Clause 29. The wearable medical device of any of clauses 25-28, wherein the supervisory circuit is configured to determine that the at least one processor has entered the failure state based on a lack of communication from the at least one processor for a predetermined time period.

Clause 30. The wearable medical device of any of clauses 25-29, wherein supervisory circuit is configured to monitor a communication state of the at least one processor.

Clause 31. The wearable medical monitoring device of any of clauses 25-30, wherein the supervisory circuit is implemented on a programmable logic device.

Clause 32. The wearable medical monitoring device of any of clauses 25-31, wherein, if the supervisory circuit detects a boot error or an operating error for the at least one processor, the supervisory circuit is configured to control the at least one processor to attempt to reboot from the current drive a predetermined number of times, and wherein, after the supervisory circuit controls the at least one processor to reboot from the current drive a predetermined number of times, the supervisory circuit is configured to control the at least one processor to boot from the alternative drive.

Clause 33. A wearable medical monitoring device, comprising: at least one processor; and a supervisory circuit configured to control the at least one processor to reboot from a current drive a predetermined number of times in response to a boot error or an operating error of the at least one processor, wherein, after the supervisory circuit controls the at least one processor to reboot from the current drive the predetermined number of times, the supervisory circuit is configured to control the at least one processor to boot from an alternative drive different from the current drive.

Clause 34. A wearable medical monitoring device, comprising: a monitor configured to monitor a physiological parameter of a subject, the monitor including a processor including a plurality of boot selection pins for setting a boot order of the processor, the boot order indicating an order in which the processor checks a plurality of ports for a drive including executable code; and circuitry configured to control one or more of the boot selection pins based on a control signal from a supervisory circuit.

Clause 35. The wearable medical monitoring device of clause 34, wherein the circuitry comprises at least one of a programmable logic device (PLD), an application-specific integrated circuit (ASIC) device, and a field-programmable gate array (FPGA device).

Clause 36. The wearable medical monitoring device of clause 34 or 35, wherein the supervisory circuit is implemented in the circuitry and comprises a watchdog timer.

Clause 37. The wearable medical monitoring device of clause 36, wherein the circuitry comprises a counter, wherein the counter is configured to increment a count based on an expiration of the watchdog timer, and wherein the circuitry is configured to control the one or more boot selection pins based on the count of the counter.

Clause 38. The wearable medical monitoring device of clause 36 or 37, wherein the circuitry is configured to send a reboot command to the processor based on an expiration of the watchdog timer.

Clause 39. The wearable medical monitoring device of clause 37, wherein the expiration of the watchdog timer is based on a communication state of the circuitry with a software application of the monitor.

Clause 40. The wearable medical monitoring device of clause 37 or 39, wherein the circuitry activates the one or more boot selection pins when the count satisfies a count threshold.

Clause 41. The wearable medical monitoring device of clause 40, wherein the circuitry controls the one or more boot selection pins to have a default value when the count does not satisfy the count threshold, and wherein the monitor is configured to check a first port in the order of the plurality of ports indicated by the boot order when the one or more boot selection pins have the default value.

Clause 42. The wearable medical monitoring device of clause 41, wherein the monitor is configured to check a next port after the first port in the order of the plurality of ports indicated by the boot order when the circuitry activates the one or more boot selection pins.

Clause 43. The wearable medical monitoring device of clause 42, wherein, for a corresponding checked port of the plurality of ports, the circuitry is configured to determine that the executable code on the drive is corrupted or a physical error exists in the drive.

Clause 44. The wearable medical monitoring device of clause 43, wherein the monitor is configured to automatically notify a remote server that the code on the drive is corrupted or the physical error exists in the drive.

Clause 45. The wearable medical monitoring device of clause 43 or 44, wherein the monitor is configured to copy a code image from a drive associated with a next port of the plurality of ports indicated by the boot order onto a drive associated with a port of the plurality of ports associated with the drive that is determined to be corrupted or have a physical error.

Clause 46. The wearable medical monitoring device of any of clauses 43-45, wherein if executable code exists on a drive associated with a current port checked by the processor, the processor is configured to execute the code.

Clause 47. The wearable medical monitoring device of any of clauses 43-46, wherein if no executable code exists on a drive associated with a current port checked by the processor, the processor is configured to check a next port of the plurality of ports in the boot order for a drive including executable code.

Clause 48. The wearable medical monitoring device of any of clauses 43-47, wherein the circuitry is configured to provide an interface between the processor and at least one other processor.

Clause 49. The wearable medical monitoring device of claim of any of clauses 43-48, where the one or more boot selection pins are hardwired directly to the circuitry.

Clause 50. The wearable medical monitoring device of any of clauses 34-49, further comprising: a medical treatment device configured to deliver a medical treatment to the subject.

Clause 51. A method of booting a wearable medical monitoring device, comprising: monitoring a state of at least one processor of the wearable medical monitoring device with a supervisory circuit when the at least one processor is configured to boot from a current drive, and controlling, with the supervisory circuit, the at least one processor to boot from an alternative drive different from the current drive based on the state of the at least one processor.

Clause 52. A wearable medical monitoring device, comprising: a monitor configured to monitor a physiological parameter of a subject, wherein the monitor is configured to communicate with a distribution node including a processor connected to a plurality of electrodes, and wherein the monitor is configured to determine if the distribution node is compatible with the monitor.

Clause 53. The wearable medical monitoring device of clause 52, wherein the monitor is configured to determine if a hardware version of the distribution node is compatible with the monitor.

Clause 54. The wearable medical monitoring device of clause 52 or 53, wherein the monitor is configured to determine if a software version of the distribution node is compatible with the monitor.

Clause 55. The wearable medical device of clause 54, wherein the monitor is configured to determine a time period to update the software version of the distribution node based on a use of the distribution node.

BRIEF DESCRIPTION OF THE DRAWINGS

These and other features and characteristics of the present disclosure, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limit of the disclosure.

Further features and other examples and advantages will become apparent from the following detailed description made with reference to the drawings in which:

FIG. 7B is a flow chart of a software downloading process according to an example of the present disclosure.

DETAILED DESCRIPTION

Figure 1:
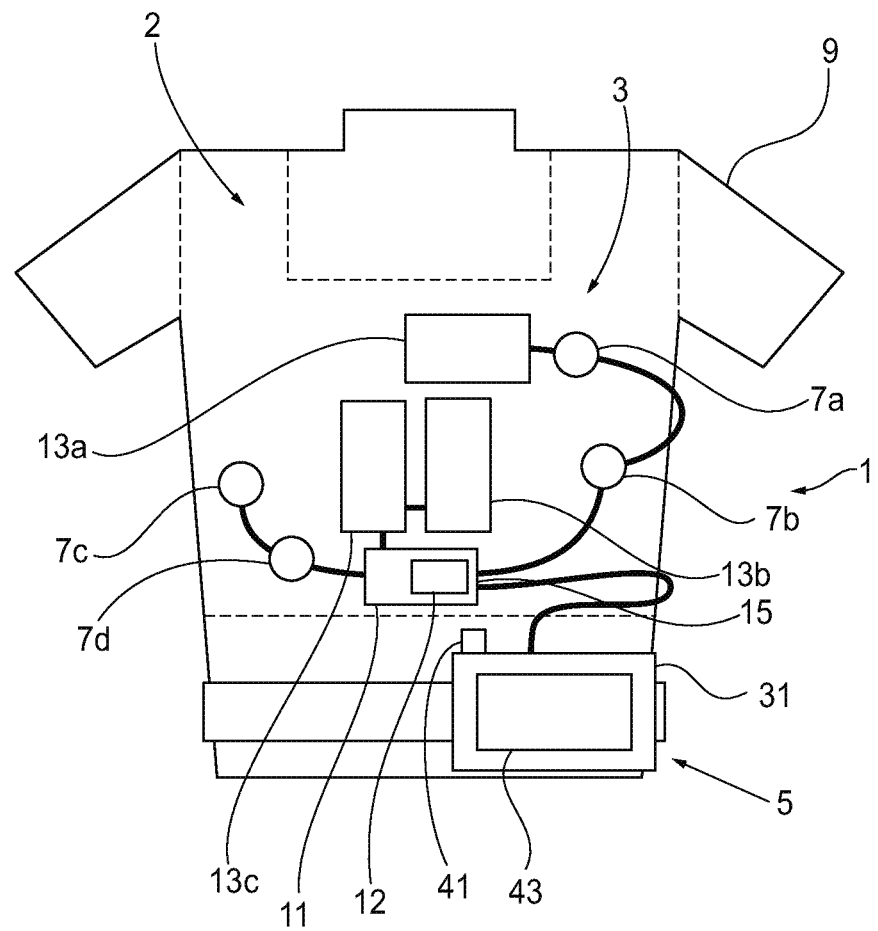
FIG. 1 shows a wearable medical device according to an example of the present disclosure.

As used herein, the singular form of "a", "an", and "the" include plural referents unless the context clearly dictates otherwise.

As used herein, the terms "end", "upper", "lower", "right", "left", "vertical", "horizontal", "top", "bottom", "lateral", "longitudinal" and derivatives thereof shall relate to the subject matter described herein as it is oriented in the drawing figures. However, it is to be understood that the presently described subject matter can assume various alternative orientations and, accordingly, such terms are not to be considered as limiting. Also, it is to be understood that the presently described subject matter can assume various alternative variations and stage sequences, except where expressly specified to the contrary. It is also to be understood that the specific devices and processes illustrated in the attached drawings, and described in the following specification, are simply examples of the subject as described herein. Hence, specific dimensions and other physical characteristics related to the examples disclosed herein are not to be considered as limiting.

For the purposes of this specification, unless otherwise indicated, all numbers expressing quantities of ingredients, reaction conditions, dimensions, physical characteristics, and so forth used in the specification and claims are to be understood as being modified in all instances by the term "about." Accordingly, unless indicated to the contrary, the numerical parameters set forth in the following specification and attached claims are approximations that can vary depending upon the desired properties sought to be obtained by the present disclosure.

Notwithstanding that the numerical ranges and parameters setting forth the broad scope of the present disclosure are approximations, the numerical values set forth in the specific examples are reported as precisely as possible. Any numerical value, however, inherently contains certain errors necessarily resulting from the standard deviation found in their respective testing measurements.

Also, it should be understood that any numerical range recited herein is intended to include all sub-ranges subsumed therein. For example, a range of "1 to 10" is intended to include any and all sub-ranges between and including the recited minimum value of 1 and the recited maximum value of 10, that is, all subranges beginning with a minimum value equal to or greater than 1 and ending with a maximum value equal to or less than 10, and all subranges in between, e.g., 1 to 6.3, or 5.5 to 10, or 2.7 to 6.1.

As used herein, the terms "communication" and "communicate" refer to the receipt or transfer of one or more signals, messages, commands, or other type of data. For one unit or component to be in communication with another unit or component means that the one unit or component is able to directly or indirectly receive data from and/or transmit data to the other unit or component. This can refer to a direct or indirect connection that can be wired and/or wireless in nature. Additionally, two units or components can be in communication with each other even though the data transmitted can be modified, processed, routed, and the like, between the first and second unit or component. For example, a first unit can be in communication with a second unit even though the first unit passively receives data, and does not actively transmit data to the second unit. As another example, a first unit can be in communication with a second unit if an intermediary unit processes data from one unit and transmits processed data to the second unit. It will be appreciated that numerous other arrangements are possible.

This disclosure relates to software and hardware improvements in medical devices. For example, the medical device can be a medical monitoring device for monitoring a patient's cardiac condition. In some implementations, the medical device can also include a therapeutic or treatment function for provide treatment to the patient based on detecting a medical condition, e.g., a cardiac arrhythmia. For example, the medical device can include an automated defibrillator and/or pacing device, such as a defibrillator and/or pacing device that can be used to, e.g., continuously monitor a patient for an extended period of time and provide treatment for a detected medical condition. In some examples, an extended-period use defibrillator can include an internal pacing device and/or defibrillator or an external ambulatory pacing device and/or defibrillator such as a wearable defibrillator. In some examples, an extended-period use defibrillator can include an in-facility defibrillator for patients that are confined to a limited space within a facility, such as, within a hospital environment, to a patient's room. In another example, a pacing device can be used to deliver a pacing pulse to a patient, for example, as intervention for symptomatic bradycardias or a complete heart block.

Example Medical Device

In an example and with reference to FIG. 1, the medical device can be configured as a wearable defibrillator, denoted generally as reference numeral 1, such as the LifeVest® wearable defibrillator available from ZOLL® Medical Corporation of Pittsburgh, Pa. and Chelmsford, Mass. The wearable defibrillator 1 can be worn by a patient and can include a garment, generally denoted as reference numeral 2, an electrode assembly, denoted generally as reference numeral 3, and a monitor, denoted generally as reference numeral 5, operatively connected to the electrode assembly 3. The garment 2 can be configured as a harness, shirt, or other apparel and is configured to permit the patient to wear the defibrillator 1. The electrode assembly 3 can be configured to be assembled within the garment 2.

Such wearable defibrillators can be typically worn nearly continuously for two to three months at a time. During the period of time in which they are worn by the patient, the wearable defibrillator 1 can be configured to continuously monitor the vital signs of the patient, to be user-friendly and accessible, to be as light-weight, comfortable, and portable as possible, and to be capable of delivering one or more life-saving therapeutic shocks when needed. Non-limiting examples of suitable wearable defibrillators are disclosed in U.S. Pat. Nos. 4,928,690; 5,078,134; 5,741,306; 5,944,669;

6,065,154; 6,253,099; 6,280,461; 6,681,003; 8,271,082; and 8,369,944; the entirety of all of which are incorporated by reference herein.

With continued reference to FIG. 1, the electrode assembly 3 includes a plurality of electrodes, such as electrodes 7a, 7b, 7c, and 7d, which are removably attached to a patient 9 when the wearable defibrillator 1 is worn by the patient 9. According to one example, the electrodes 7a, 7b, 7c, and 7d are configured to receive ECG signals from the patient 9. For instance, the electrodes 7a, 7b, 7c, and 7d can be positioned on the patient 9 to receive ECG signals from a front-to-back channel and from a side-to-side channel. For example, the front-to-back (FB) channel can include one of electrodes 7a, 7b, 7c, and 7d positioned on the chest of the patient 9 and another one of the electrodes 7a, 7b, 7c, and 7d positioned on the back of the patient 9. For example, the side-to-side (SS) channel includes one of the electrodes 7a, 7b, 7c, and 7d positioned on the left side of the chest and another one of the electrodes 7a, 7b, 7c, and 7d positioned on the right side of the chest of the patient 9. In some examples, the electrodes 7a, 7b, 7c, and 7d can be operatively connected to a distribution node 11 of the electrode assembly 3.

In some implementations, the electrode assembly 3 can also comprise therapy pads 13a, 13b, and 13c operatively connected to the distribution node 11. The therapy pads 13a, 13b, and 13c can be configured to deliver one or more life-saving therapeutic shocks when needed. In some examples, the electrode assembly 3 can also include other sensing electrodes and devices (not shown) such as, but not limited to, heart beat sensors, accelerometers, and sensors capable of measuring blood pressure, heart rate, thoracic impedance, respiration rate, heart sounds, acoustic sensors, audio transducers, and the activity level of the subject. The electrode assembly 3 can further comprise a tactile stimulator 12, such as a vibrator, positioned within the distribution node 11 to provide tactile stimulation to the patient 9 as described in greater detail hereinafter.

The monitor 5 can be operatively connected to one or more of the therapy pads 13a, 13b, and 13c and electrodes 7a, 7b, 7c, and 7d via, e.g., a trunk cable 15 or any other suitable cable or connection device. Wiring or other connection devices can be used to connect at least one portion of the distribution node 11 to the electrodes 7a, 7b, 7c, and 7d and therapy pads 13a, 13b, and 13c. Alternatively, the monitor 5 can be operatively connected to one or more of the electrodes 7a, 7b, 7c, and 7d, therapy pads 13a, 13b, and 13c, and distribution node 11 by a wireless connection or a combination of wireless and wired connections.

The distribution node 11 can be configured to obtain ECG data from the electrodes 7a, 7b, 7c, and 7d, digitize this data, and transfer this data to the monitor 5. Accordingly, the distribution node 11 can include a processor, such as a belt node processor (BNP) 17 (see FIGS. 3 and 4), operatively connected to electrodes 7a, 7b, 7c, and 7d and configured to receive signals representing the ECG of the patient 9 from the electrodes 7a, 7b, 7c, and 7d. The BNP 17 can communicate with the monitor 5 via a Controller Area Network (CAN) bus 19 (see FIGS. 3 and 4) or any other suitable bus. The BNP 17 is also configured to sense whether one or more of electrodes 7a, 7b, 7c, and 7d have fallen off the patient's body, to control the tactile stimulator 12, and to fire the electrode gel interface for providing electrolytic gel to the therapy pads 13a, 13b, and 13c when a request is received from the monitor 5.

Figure 2:
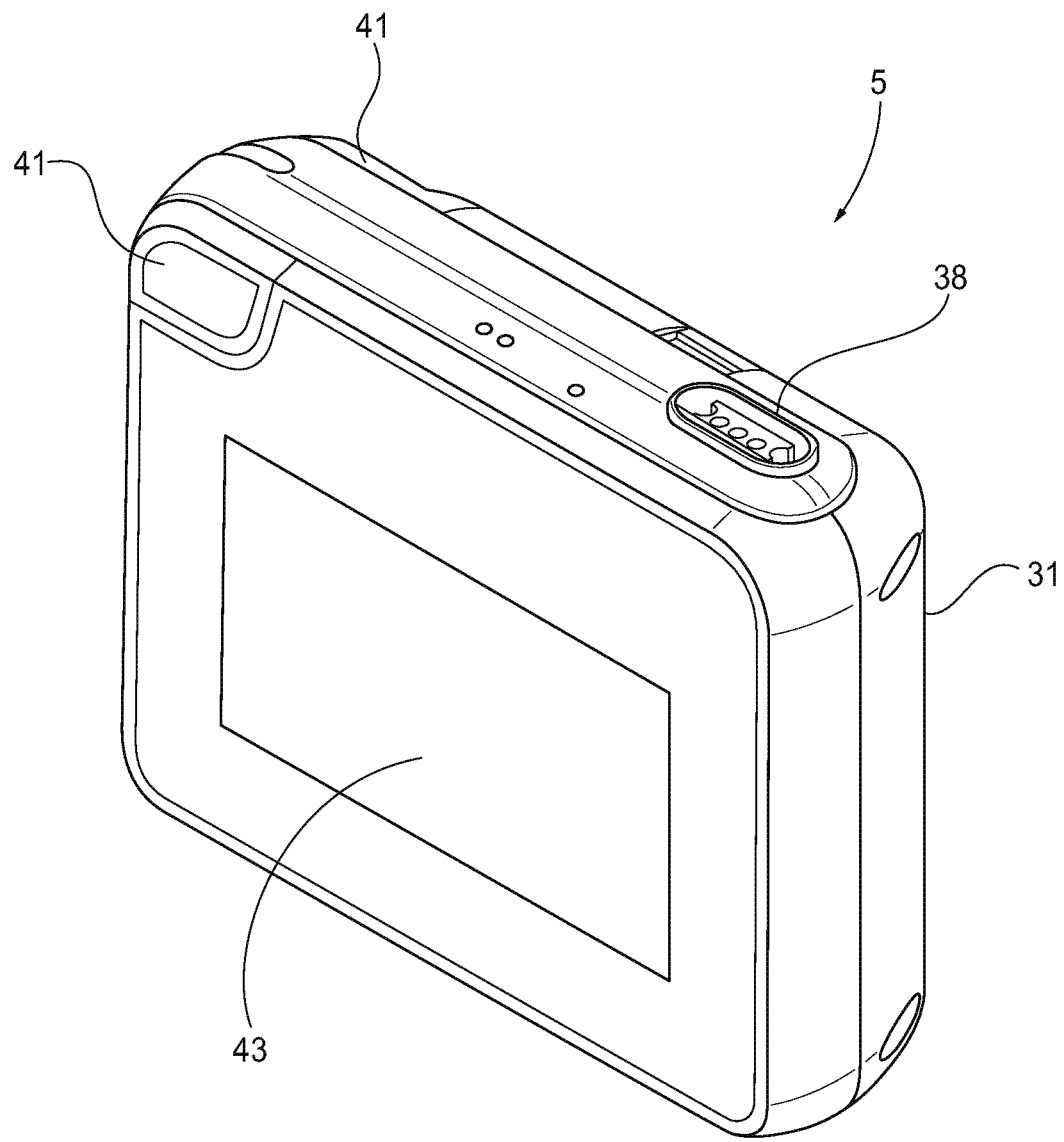
FIG. 2 shows a front perspective view of a monitor for a wearable medical device according to an example of the present disclosure.

With reference to FIG. 2 and with continuing reference to FIG. 1, the monitor 5 can include an external housing 31 having a port 38 to which the ECG electrodes 7a, 7b, 7c, and 7d and therapy pads 13a, 13b, and 13c of the electrode assembly 3 are operatively coupled to the monitor 5 via the trunk cable 15. The monitor can include one or more batteries, such as a rechargeable and removable battery (not shown) positioned within a battery housing. The battery has sufficient capacity to allow the wearable defibrillator 1 to administer one or more therapeutic shocks as well as provide power to all of the internal components of the defibrillator 1. The external housing 31 further comprises at least one, and for example, a pair of patient response buttons 41 positioned, for example, in the top left corner of the housing 31. The external housing 31 of the defibrillator can also include a display screen 43 for providing information to the patient 9 and for providing a user input device to the patient 9. Further details of the monitor 5 can be found in U.S. patent application Ser. No. 14/448,997, entitled "Indicators on a Wearable Medical Therapy Device", which is hereby incorporated by reference in its entirety.

System Architecture of an Example Medical Device

Figure 3:
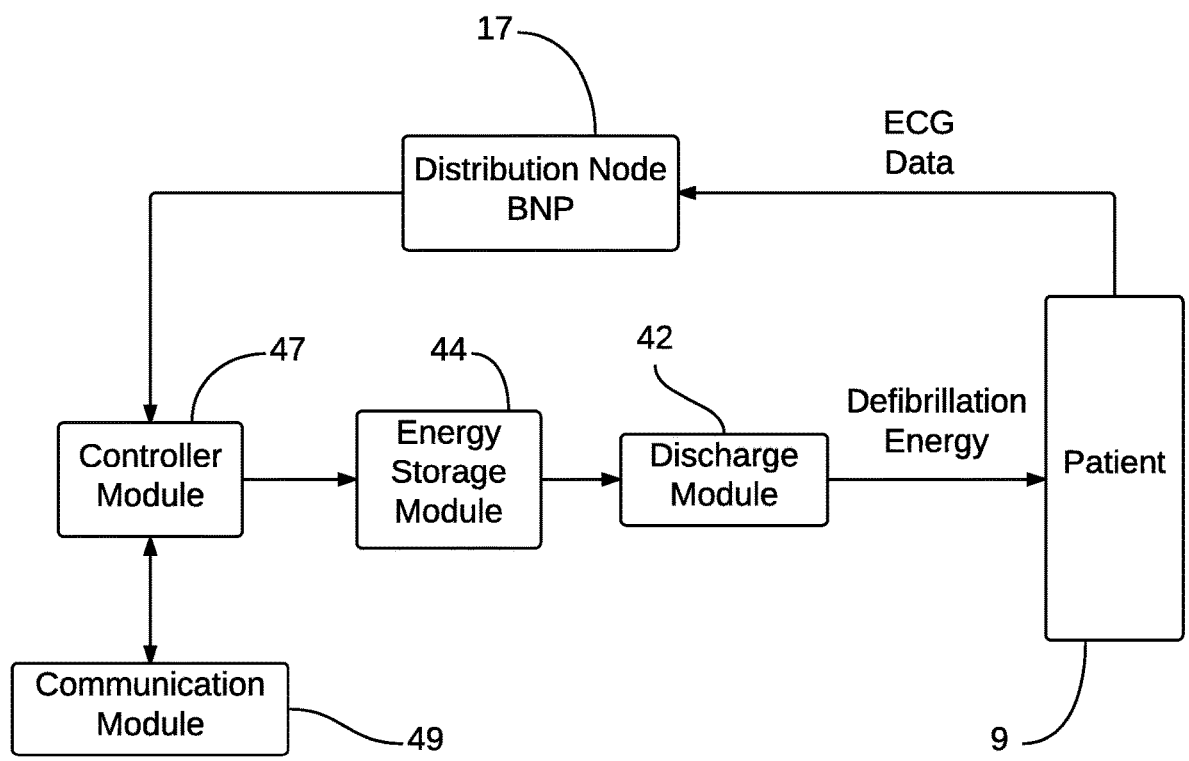
FIG. 3 is a block diagram illustrating the manner in which functional components of the wearable medical device interact according to an example of the present disclosure.

With reference to FIG. 3 and with continuing reference to FIGS. 1 and 2, the functional components of the monitor 5 can be provided within the external housing 31 of the monitor 5. In one example, the functional components can be provided on a distributed printed circuit board as disclosed in U.S. patent application Ser. No. 14/448,857. In one example, the functional components can comprise a discharge module 42, an energy storage module 44, a controller module 47, and a communication module 49. For example, the discharge module 42 can be configured to selectively deliver an energy pulse to the patient 9. The energy storage module can be operatively connected to the discharge module 42. The controller module 47 can be operatively connected to the energy storage module 44 and can be configured to control the delivery of the energy pulse to the patient 9. The communication module 49 can be operatively connected to the controller module 47.

Figure 4:
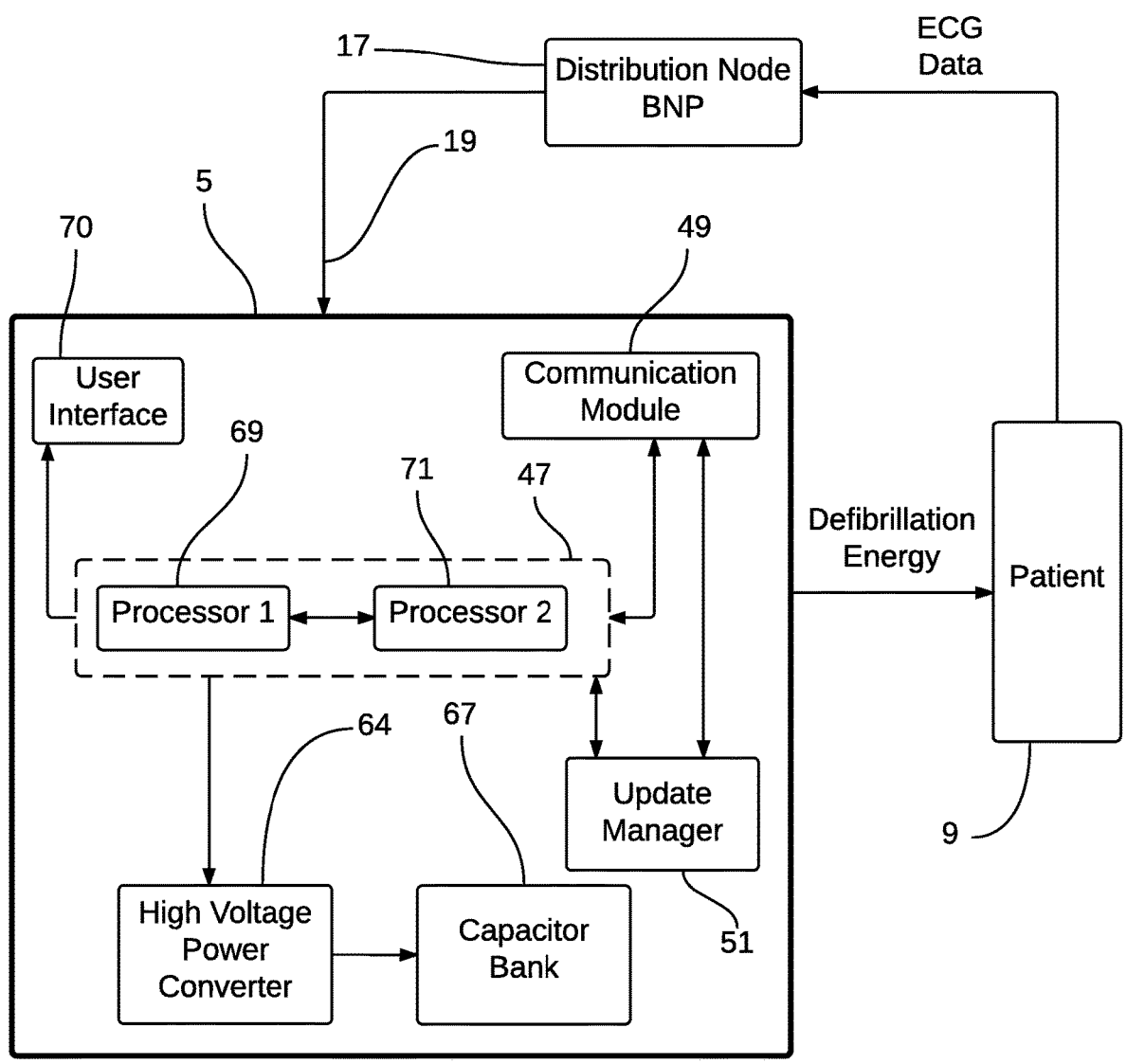
FIG. 4 is a block diagram of a wearable medical device according to an example of the present disclosure.

In one example, the energy storage module 44 can include a high voltage power convertor 64 (shown in FIG. 4) and a capacitive device, such as a bank of capacitors 67 (shown in FIG. 4). The discharge module 42 can include at least one high-voltage switch (not shown) and can be configured to selectively deliver an energy pulse stored in the energy storage module 44 to the patient 9 based on a signal from the controller module 47. The energy pulse is sent from the discharge module 42 through the port 38 (shown in FIG. 2) to the therapy pads 13a, 13b, and 13c.

For example, a biphasic waveform is delivered to the patient 9 by switching the at least one high voltage switch of the discharge module 42. The operation of the pulse delivery system can be dynamic and depend on the patient body impedance while the pulse is being delivered. For example, an amount of energy delivered can be held constant while varying the duration of the first phase and the second phase. In another example, a monophasic waveform can be delivered to the patient depending on the patient's condition.

The controller module 47 can include one or more processors for performing certain functionalities of the wearable defibrillator 1. The controller module 47 includes processors and related circuitry for implementing critical and non-critical functionality of the defibrillator 1. For example, such device functionality is carried out by one or more software modules stored in a memory unit and executed by the processors. By way of example, one or more of the processors can execute instructions configured to monitor a patient's cardiac status and provide defibrillation when deemed necessary. The processors can also provide additional functionality, including but not limited to: conducting device-administered patient tests; collecting, storing, analyzing, and transmitting cardiac data and related metrics, patient physical activity, data trends, heart sounds information, among other similar and related functionality. Such software modules can be updated occasionally (e.g., on a predetermined schedule) in accordance with the principles described herein. For example, the defibrillator 1 can be in communication with a remote server (e.g., an update server) that includes a software repository including one or more software update modules or patches configured to be transmitted from the remote server to the monitor 5 for verification and installation on the memory unit associated with the processors. Thus, the techniques described herein in additional detail provide a process for updating the software modules associated with the and executed by the processors.

With reference to FIG. 4, and with continuing reference to FIGS. 1-3, one example of the controller module 47 can include at least a first processor 69 and a second processor 71. In some examples, the first and second processors 69, 71 can be two cores of a single processor. In an example, the first processor 69 and the second processor 71 can be configured to function as disclosed in U.S. Pat. No. 8,904,214, entitled "System and Method for Conserving Power in a Medical Device", which is hereby incorporated by reference in its entirety.

In an example, the controller module 47 can be operatively connected to a user interface 70, the high voltage power convertor 64, and the bank of capacitors 67. Such a configuration allows at least one of the first processor 69 and the second processor 71 to be capable of providing output to a patient 9, for example through the display screen 43, and accept input from the patient 9, for example from response buttons 41, as well as provide instructions to the high voltage power converter 64 to deliver a therapeutic shock to the patient 9. For example, the first processor 69 and the second processor 71 can be used to provide certain functionality within the wearable defibrillator 1 such as, but not limited to: high voltage converter control; discharge module control; execution of therapy pulse synchronization (e.g., synchronizing the pulse delivery to avoid delivering a pulse on a T wave); ECG acquisition from the CAN bus 19; ECG monitoring and arrhythmia detection; user interface control; treatment sequencing; audio message generation; and data communications and storage. An example of the methods used to detect abnormal heart rhythms can be found in U.S. Pat. No. 5,944,669, entitled "Apparatus and Method for Sensing Cardiac Function, which is assigned to the assignee of the present application and which is hereby incorporated by reference in its entirety.

In some implementations, the BNP 17 can be operatively connected to the controller module 47. The BNP 17 can act as an ECG data acquisition engine for the controller module 47 via the CAN bus 19 as described hereinabove.

In one example and as shown in FIG. 4, the communication module 49 can be controlled by the processors 69, 71 of the controller module and provides various devices for communicating information to and from the monitor 5. For instance, the communication module 49 can include a GPS transceiver, a Bluetooth transceiver, a Wi-Fi modem 200 (see FIG. 7A), and a cellular modem 202 (see FIG. 7A). The communication module 49 is configured to communicate with a remote server provided via the cellular modem 202. Alternatively, if cellular communication capabilities are not available, the communication module 49 can communicate with the remote server via the Wi-Fi modem 200.

Monitor 5, as illustrated in FIG. 4, can also include an update manager 51. As discussed above, the individual processors 69, 71 in control module 47 operate various functions by executing one or more instructions contained in various software modules. Based upon the length of time the monitor is used, and potential patches, error fixes or other similar software updates that can be developed, the control module can be updated to include a new software module, a software patch and/or upgrade to an existing software module.

The update manager 51 can be configured to facilitate updating/upgrading the software modules. Depending upon the design of the monitor 5 and its internal components, as well as the functional capabilities of those components, the update manager 51 can be implemented as a processing device configured to execute a set of localized instructions for monitoring software associated with the monitor 5 (e.g., software modules and instructions executed by the processors 69, 71).

Similarly, the update manager 51 can be configured to establish an operable connection to and communicate with a remote server (e.g., an update server configured to store software updates and patches associated with the software modules and instructions executed by the processors 69, 71. As shown in FIG. 4, the update manager 51 can establish such an operable connection with a remote server via the communication module 49. After establishing the operable connection, the update manager 51 can facilitate the updating of one or more of the software modules according to, for example, the update process described below in regard to FIG. 7B.

It should be noted that the update manager 51, as shown in FIG. 4, is shown as a separate component by way of example only. In another example, the update manager 51 can be a software module containing instructions for execution by one of the processors 69, 71. In such an example, when one of processors 69, 71 is not performing a critical function, that processor can execute a set of update instructions associated with the update manager 51 to perform an update process. For example, one of the processors 69, 71 can perform the update process as described below in regard to FIG. 7B. In another example, the update manager 51 can be implemented as a bootable drive image. The monitor 5 can be configured to, upon appropriate input from an authorized user of the medical device 1 (e.g., a medical care provider or device technician), boot directly from the drive image of the update manager 51. The monitor 5 can then directly execute a software update per instructions contained within the update manager 51 without additional input.

Additionally, it should be noted that the update manager 51, as described above and shown in FIG. 4, is described as using the communication module 49 for establishing a connection to the remote server is shown by way of example only. Based upon the design and implementation of the update manager 51 (e.g., if the update manager 51 is implemented as a dedicated processing device), the update manager 51 can include one or more communication interfaces for directly establishing the operable connection with the remote server.

Supervisory Circuit Overview

Figure 5:
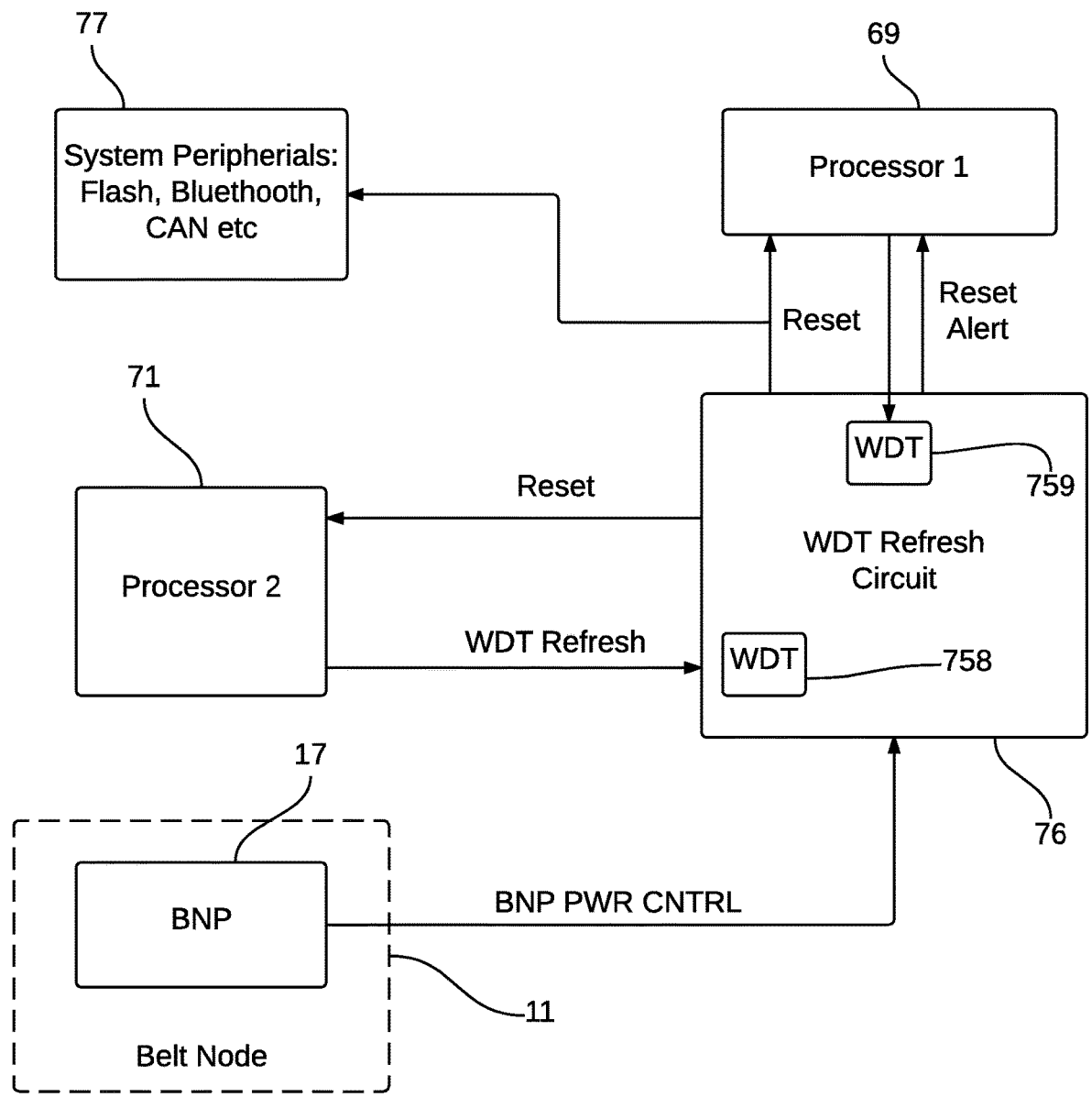
FIG. 5. is a block diagram of a supervisory, e.g., watchdog timer (WDT) scheme for a wearable medical device according to an example of the present disclosure.

With reference to FIG. 5 and with continuing reference to FIGS. 3 and 4, in one example, the controller module 49 can include circuitry or circuit 76, e.g., implemented on a programmable logic device (PLD), to provide, among other things, a supervisory circuit function as described herein. The example use of a PLD to illustrate the processor supervisory circuit function, as well as the redundant media booting discussed hereinafter, is not to be construed as limiting. Any suitable electronic circuitry, hardware configuration or device can be used to implement the processor supervisory function. For instance, a field-programmable gate array (FPGA), an application-specific integrated circuit (ASIC), or any other suitable electronic hardware or integrated circuit can be used.

The circuit 76 can be configured to provide interfacing support and input/output translations between the first processor 69, the second processor 71, and various peripherals 77. For example, the peripherals 77 can include the patient response buttons 41, shared memory interface, the CAN controller, system power control, and the communication module 49. As noted, the circuit 76 can be configured to implement a processor supervisory function. For example, such a supervisory function can be a watchdog timer (WDT) function 75*a*, 75*b*.

In general, the supervisory function can be a supervisory circuit 300 (see FIG. 8) that monitors one or both of the first processor 69 and the second processor 71. In some cases, two or more supervisory circuits 300 can be implemented, each responsible for two or more corresponding device processors. For example, separate supervisory circuits 300 can monitor one of the three device processors described hereinabove (e.g., the BNP 17, the first processor 69, or the second processor 71). For example, the first processor 69 and the second processor 71 can be required to periodically service the WDT 75*a*, 75*b* function to prevent a timeout from occurring.

In some implementations, one of the processors 69, 71 can act as a master control processor and have control over the reset and startup of the other one of the processors 69, 71. In the event of a watchdog timeout of the controlled processor, the master processor can be notified to take action by executing an orderly restart of the system to restore function. If the master processor fails to perform the required WDT servicing, the circuit 76 can automatically restart the system to restore functionality.

In a typical monitoring operation, when one or both of processors 69, 71 executes, the one or both processors 69,71 can initiate contact with the BNP 17 and begin execution of the arrhythmia detection algorithm. ECG data received from the BNP 17 can be analyzed by the arrhythmia detection algorithms and written into a memory (not shown) for short or long-term storage. One or both processors 69, 71 can include software (e.g., implementing a state machine) that responds to various events generated external to the processor. An example of one of these control signals can be the patient response buttons 41. In an implementation, the processors 69, 71 can also handle user interaction functions. For example, the display screen 43 and audio output interfaces can be used for these functions.

Operation of the Example Medical Device

Figure 6:
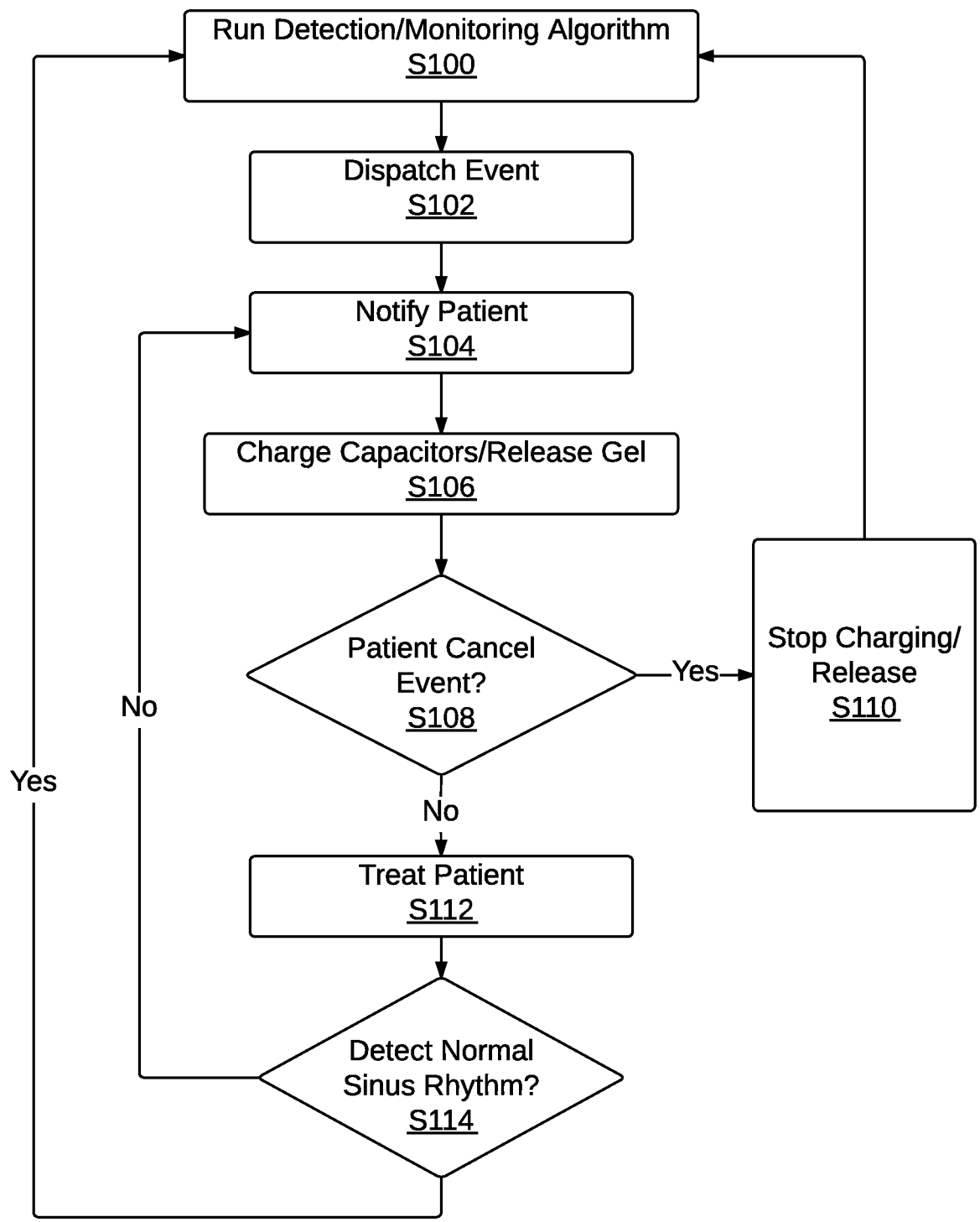
FIG. 6 is a flow chart of a method of operation of a wearable medical device according to an example of the present disclosure.

With reference to FIG. 6, a description of the manner in which the monitor 5 operates when an abnormal event is detected by the detection algorithm of one or both of the processors 69, 71 will be described. Initially, at least one of the processors 69, 71 is running the detection (and/or monitoring) algorithm and detecting normal sinus rhythm at stage S100. In one example, one of the processors 69, 71 can be running the detection algorithm and the other of the processors 69, 71 can be in a low-power sleep state. When the detection algorithm detects a VT or VF rhythm type, it can dispatch an event to, e.g., initiate a notification sequence, to another function that is run on at least one of the processors 69, 71 at stage S102. The state machine exits the normal sinus rhythm monitoring state when the event is received and transitions to a notification state at stage S104 that begins the patient notification sequence to provide stimuli to the patient to make the patient aware that an event has been detected and starts a capacitor charge cycle at stage S106.

In some examples, after the capacitors are fully charged, conductive gel can be released followed by a gel wetting period to reduce transthoracic impedance. In some examples, the conductive gel can be released substantially simultaneously with the charging of the capacitors, or configured to occur towards the end of the charging period.

At any point after the notification at stage S104, the patient can cancel the treatment sequence by pressing the response buttons 41 and the system acknowledges the patient response and stops charging capacitors 110. This is shown by stages S108 and S110. If the patient does not respond to the alarms at stage S108, the state machine can issue a command to at least one of the processors 69, 71 to fire the defibrillator and treat the patient at state S112. In an implementation, the at least one processor 69, 71 can detect a sinus rhythm after the firing of the defibrillator at stage S114 to determine if the defibrillation was successful and send an event notification to the state machine. In an implementation, the at least one processor 69, 71 can detect either a normal sinus rhythm or a VT rhythm after the firing of the defibrillator at stage S114 to determine if the defibrillation was successful. If the defibrillation was not successful, an event notification is sent that returns to the patient notification sequence to provide stimuli to the patient to make the patient aware that an event has been detected and restarts a capacitor charge cycle at stage S106. One of the processors 69, 71 can continue to run the detection (and/or monitoring) algorithm during charging of the capacitor and/or release of the gel for a VT rhythm. If the defibrillation was successful and a sinus rhythm is detected, at least one of the processors 69, 71 can return to running the detection (and/or monitoring) algorithm and detecting normal sinus rhythm at stage S100.

Software Downloading

Below is described an example software download mechanism for use in a medical monitoring device. For illustration purposes, the example software download mechanism is described in connection with the wearable medical defibrillator 1 above, and in the context of the system and software architecture described above. However, it is to be understood that the techniques described below can be implemented on any other medical device (including devices having different system and software architectures to that described above). Moreover, it is to be understood that the mechanism can assume various alternative orientations and, accordingly, such descriptions herein are not to be considered as limiting.

In some examples, the medical device 1 can download data such as software updates through, for example, the update manager 51. More specifically, the software update data can include new firmware or software to be deployed, firmware or software upgrades and/or changes (e.g., monitor software updates, BNP updates, and/or other device software or firmware updates), new or changes and/or updates to device settings and configuration parameters (e.g., the monitor's programmed settings such as rate thresholds and energy settings), and new or changes and/or updates to critical and non-critical data for use in operation of the monitor 5 (e.g., predetermined device-guided patient training modules).

Figure 7A:
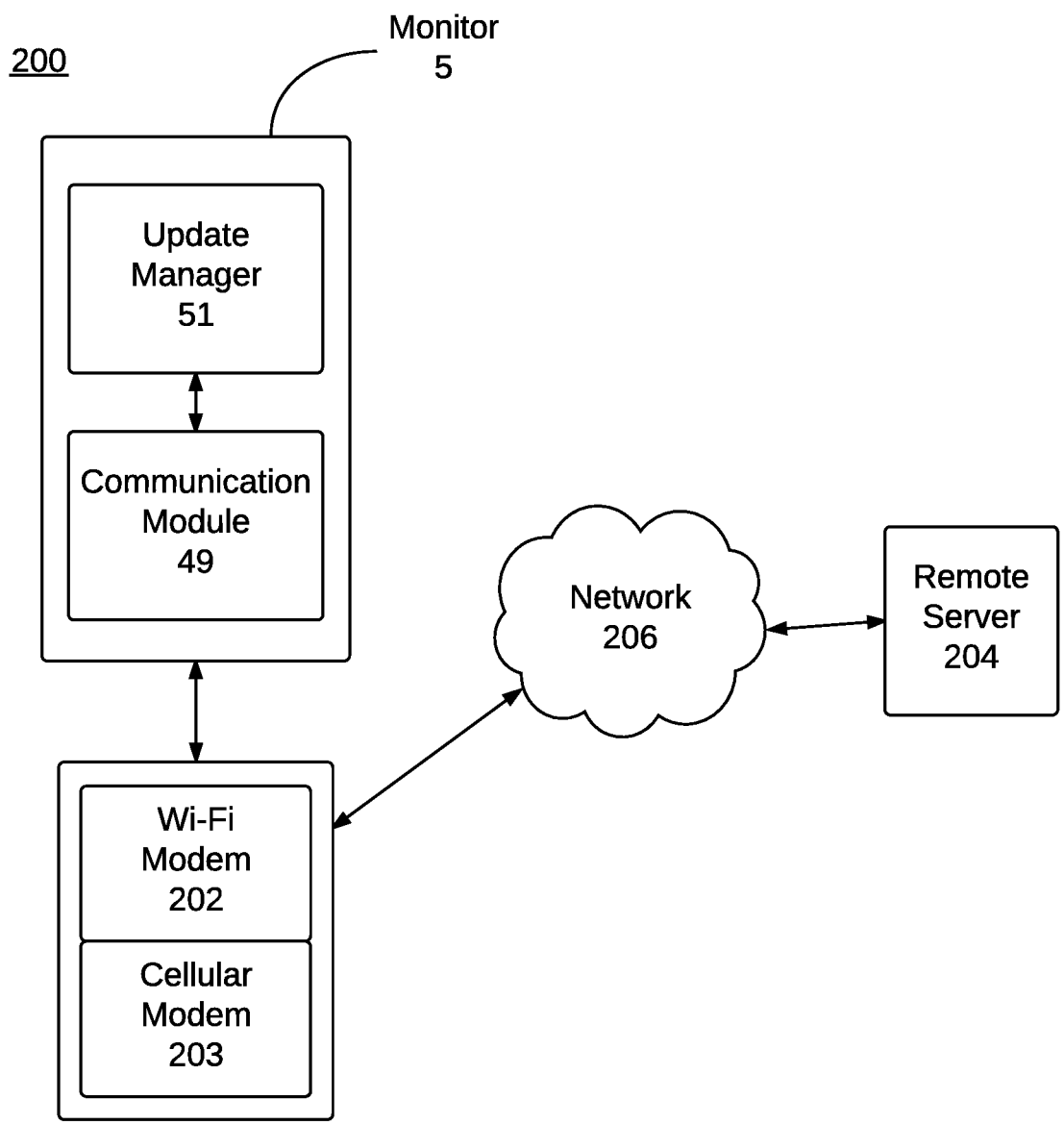
FIG. 7A is a block diagram of a software downloading system according to an example of the present disclosure.

FIG. 7A depicts a sample system 200 for downloading data such as a software update to a device such as medical device 1 as described herein. The update manager 51, as noted above, can establish or facilitate establishment of an operable connection to a remote server 204 via a network 206. Depending upon the location and communication capabilities of the various devices, the network 206 can be a local area network such as a Wi-Fi network in a doctor's or other similar medical service provider's office. Alternatively, the network 206 can be a wide area network such as the Internet.

Depending upon the implementation of the update manager 51, the operable connection between the update manager 51 and the remote server 204 can be established by the communication module 49 through one of a Wi-Fi modem 202 or a cellular modem 203. Depending upon the design and functional capabilities of the monitor 5 of the medical device 1, the Wi-Fi modem 202 and/or the cellular modem 203 can be integrated into the monitor. In an example where the monitor 5 does not include any wide-area network capabilities, the Wi-Fi modem 202 and the cellular modem 203 can be integrated into a standalone device that the monitor is configured to interact and communicate directly with, such as a base station.

FIG. 7B depicts a sample process flow for downloading data such as a software update. It should be noted that, though the process as illustrated in FIG. 7B is directed to downloading a software update, the process can be expanded to include additional data related to or integral for the operation of the medical device 1. It should also be noted that, while specific components as described above are discussed below regarding the process flow as shown in FIG. 7B, this too is by way of example and the functions and techniques as described in FIG. 7B can be implemented and performed by various other components of the medical device 1.

As shown in FIG. 7B, the update manager 51 can check 700 for software updates at the remote server 204. The update manager 51 can periodically check for software updates and/or check for software updates in response to a prompt from the patient or a user such as a medical service provider. In another implementation, the remote server 204 can automatically notify the update manager 51 when a software update for the medical device 1 is available. The remote server 204 can receive the current software version of the medical device 1 and determine if updated software is available for the medical device 1. In some implementations, if updated software is available, the remote server 204 can notify the patient or a user via the monitor 5 of the medical device 1, such as by providing an alert via display screen 43.

The update manager 51 can download 702 the software update data from a remote server 204 based upon the operational state of the medical device 1 and/or the remote server 204. If the remote server 204 is unavailable or already servicing a high volume of requests, the update manager 51 may automatically switch to a different server (e.g., a mirror server) based upon the operational state of the remote server 204. Alternatively, the remote server 204 can automatically cause the download to the update manager 51 to be routed through a different server in such circumstances. The update manager 51 can download the data through the Wi-Fi modem 202 or the internal cellular data modem 203. The update manager 51 can download the data via the network 206. In some examples, and to the extent that data needs to be sent from the medical device 1 to the remote server 204, such data can be transferred from the monitor 5 to the remote server 204 through, for example, a secure Virtual Private Network (VPN) or any other suitable network.

As described in more detail below, the update manager 51 and/or the remote sever 204 can be configured to determine and schedule a time period to download the data from the remote server 204 and/or a time period to install a software update or process downloaded data based on a current or planned future use of the wearable medical device 1, operating parameters of the wearable medical device 1, cellular data usage and limits of the cellular data modem 203, and/or physiological parameters of the subject.

For example, a user (e.g., a patient, a service representative, or any other authorized personnel) can program a predetermined time period for downloading the data and/or performing the installation.

Referring again to FIG. 7B, the update manager 51 and/or the remote server 204 (e.g., a server-side action or an operation) can determine and schedule 702 a time period for downloading the software update based on a current operational state and/or projected operational state of the medical device 1. For example, the update manager 51 can determine that resources for facilitating the download of the software update are performing another task for a set period of time. More specifically, the communication module 49 can currently be transmitting operational data related to usage patterns and related statistics. In such a scenario, the update manager 51 can schedule 702 the software download at a time when the communication module 49 is not being used for another task. Additionally, the current operational state of the remote server 204 can impact the determination of when to download the software update. For example, if the remote server is currently handling a high amount of traffic, is down for maintenance or otherwise unavailable, the software update download can be scheduled at a time the remote server 204 will be able to perform a transfer of the software update to the update manager 51.

The update manager 51 can download 704 the software update at the scheduled time. Based upon the network connection(s) available, the update manager 51 can download the update from the remote server 204 through one of the Wi-Fi modem 202 or cellular modem 203. After downloading, the update manager 51 can verify the download completed successfully and locally store the downloaded software update at, for example, a memory associated with one of processors 69, 71. After verification, the update manager 51 can schedule 706 the software update installation during non-critical operation of the monitor. As before with scheduling the download, the update manager 51 can determine that the current operational state of the monitor 5 indicates that resources for facilitating the installation of the software update are performing another task for a set period of time. For example, one or both of processors 69, 71 can be currently executing a critical task that preempts the installation of the software update. More specifically, one or both of processors 69, 71 can be monitoring one or more signals received from a patient wearing the medical device 1 and analyzing the signal(s) to determine if any further action should be taken (e.g., defibrillation).

If the update manager 51 does determine the current operational state of the monitor 5 indicates that resources for facilitating the installation of the software update are available, or will be available at a particular time, the update manager 51 can schedule 706 the software update installation. The update monitor 51 can then install 708 the software update as appropriate at a time when the monitor 5 is not performing any critical operations. As noted above, the software update can include updates to critical or non-critical software modules associated with the operation of the monitor 5 and, as such, can be installed as appropriate to a specific memory device or processor such that, upon the next occasion that instructions associated with that software module are loaded and executed by a processor, the updated software and instructions are loaded and executed. Additional functions such as installation verification and, if necessary, redundant booting are described below in greater detail.

It should be noted that, as described above in regard to FIG. 7B, the process for downloading and installing the software update is facilitated by the update manager 51. As noted above, in some implementations the update manager 51 can be a standalone processor configured to perform at least the specific functions related to downloading and installing the software update as noted above. Alternatively, the update manager 51 can be a software module or bootable drive image containing instructions that are executed by one of the processors 69, 71 associated with the monitor 5.

In a specific example, one or more of processors 69, 71 can include, or be configured to access, a memory having two primary partitions. A first partition can be labeled as a boot partition that includes a current version of the software for the monitor 5 to perform its intended functionality. The second partition can be labeled as an update partition. The software manager 51 can be configured to facilitate downloading and installation of a software update on the update partition. Once the software update is downloaded and installed, and the update manager 51 verifies the installation, the functionality of the individual partitions can be reversed. For example, the update manager 51 can relabel the second partition as the boot partition such that the monitor 5 will be running the updated software when next booted. Similarly, the update manager 51 can relabel the first partition as the update partition. The update manager 51 can be configured to relabel the partitions by, for example, updating a pointer or other indicator used by the monitor when booting to identify which partition to access during booting. Additionally, in a two-partition arrangement, the monitor 5 can include a redundant booting scheme to, in the event of errors of other problems being associated with the software update, boot using an older version of the software. Such a redundant booting process is described below in additional detail.

Additional examples of implementation of the process as shown in FIG. 7B are discussed below in greater detail. For example, if the update manager 51 and/or the remote server 204 determines that the medical device 1 is currently monitoring the patient or performing some other critical function, the update manager 51 and/or the remote server 204 can temporarily delay, cancel indefinitely, or only partially carry out the software update (e.g., download and unpack the installation package, but not install the update, or only install a portion of the update that does not affect or implicate the critical function). Accordingly, based upon the operational state indicative of a critical function being performed by the medical device 1, the downloading and/or installation of the software update can be delayed. Such an operational state indicative of a critical function can include a device function and/or operation that can be impacted by the proposed software update. For example, a critical function can be an operation where the device is being charged, and the proposed software update is an update to the battery charging software. Another critical function can be an operation related to an application of a pacing pulse to a patient, and the proposed software update is an update to the pacing pulse software. In some examples, a critical function can be any function that is required for determining, preparing, and/or applying a treatment to a patient and/or required for determining, preparing, and/or notifying the patient and/or another party of a current or future medical event for the patient, and the proposed software update is an update to software for the function.

Similarly, if the update manager 51 and/or remote server 204 determines that the medical device 1 will, at a predetermined future time (e.g., in a next few minutes or hours), be monitoring the patient or performing a critical function related to monitoring or analyzing the current condition of the patient, then the monitor can temporarily or indefinitely suspend the update, or only partially carry out the update.

Alternatively, if the update is a minor update to a Bluetooth or other wireless module that would not have an impact on the monitoring function or other critical function, the update manager 51 and/or the remote server 204 can proceed with the minor update. A number of factors can be considered in making such a determination. For example, such factors can include, a time needed for the download, unpacking, and installation, a size of the update, a relationship of the update type to the current and/or future function of the medical device 1. In this manner, the medical device 1 software can be updated without interrupting or interfering with critical functions of the medical device 1.

As another example, if the update is to a configuration change in the settings relating to a patient training module, and it is determined that such an update would not have an impact on any critical functions of the device such as the monitoring, notification, charging, and therapy delivery systems, then the update can be allowed to proceed.

In some examples, if a time needed for the download, unpacking, and installation of a software update and/or a size of the software update exceeds a predetermined threshold or would otherwise interfere with a patient's use of the medical device 1, the update manager 51 and/or the remote server 204 can temporarily delay, cancel indefinitely, or only partially carry out the software update (e.g., download and unpack the installation package, but not install the update, or only install a portion of the update having an installation time or size that does not exceed the threshold or that is selected by the patient).

For example, such a time threshold can be stored as a configurable parameter set by a user or automatically determined by system capacity and speed, and can be expressed in seconds and/or minutes. In an implementation, the time threshold can be set to a default value, which can then be varied. As an illustration only, such a time threshold can be set to be 60 seconds, or one minute. That is, if it is determined that the time needed for the download, unpacking, and installation of a software update would exceed 60 seconds, then the update manager 51 and/or the remote server 204 can temporarily delay, cancel indefinitely, or only partially carry out the software update (e.g., download and unpack the installation package, but not install the update, or only install a portion of the update having an installation time that does not exceed the time threshold that is selected by the patient).

Similarly, a size threshold can be stored as a configurable parameter set by a user or automatically determined by system capacity and speed, and can be expressed in typical data storage units such as MB or GB. In an implementation, the size threshold can be set to a default value, which can then be varied. As an illustration only, such a size threshold can be 1 GB. While example time and size thresholds are described here for illustration only, it should be understood that these thresholds can be any value set by a user or the system.

In some implementations, the user and/or the system can provide different download settings corresponding to different types of software updates. For example, the user can set the thresholds to be 2 minutes and 2 GB respectively where the updates relate to a functional firmware or software update, such as an update to a wireless module software, and 30 seconds and 512 MB respectively where the updates are changes to configuration settings of the device such as a scheduled time and content information for delivery of a device-guided training module. In some examples, if the software update is a software update for a function that is currently in use, e.g. a function that is currently being executed or loaded into memory, or a function that is scheduled for future execution during a time needed for download, unpacking, and/or installation of the update, the update manager 51 and/or the remote server 204 can temporarily delay the software update until the function that would be affected or implicated is no longer in use, cancel indefinitely the software update, or only partially carry out the software update (e.g., download and unpack the installation package, but not install the update, or install only a portion of the update that does not affect or implicate a function currently in use or scheduled for use).

In some examples, if the software update is an update or fix for one or more critical errors, flaws, failures or faults in a software program that can cause a failure of the medical device 1 or a danger to the patient, the update manager 51 and/or the remote server 204 can override a delay that would otherwise be implemented with respect to installation of the update. For example, an update to a critical function or a function that is currently in use, which would typically be delayed by the update manager 51 and/or the remote server 204, can be downloaded, unpacked, and installed if the update manager 51 and/or the remote server 204 determines that the update is required to fix a critical error in a function or operation of the device. In an example, instead of overriding the delay, the device can alert or notify the patient through audible, visual, or tactile art mechanisms that such an update may be necessary and advise the patient to seek help or plan for having the update to be deployed in a safe and effective manner. For example, the patient may be advised to call a service center for ensuring that such an update is safely and effectively carried out. Alternatively, the patient may be advised to visit his or her health care facility to seek assistance with the update, as described in further detail below.

Alternatively, if the update manager 51 and/or the remote server 204 determines that the update is not an update required to fix a critical error, the monitor 5 and/or the server 204 can temporarily delay, cancel indefinitely, or only partially carry out the software update (e.g., download and unpack the installation package, but not install the update) based on one or more of the factors described herein.

The data download control can provide call collision management to prevent heavy load on the remote server and/or the Internet/POTS connection. In order to spread the load of calls out among the patient population, each patient/monitor 5 can be assigned a random download period, e.g., a particular day of the week that the update manager 51 begins attempting data downloads. Each day is grouped into 'bins' of hours. The length of each bin is a programmable parameter ranging from 1 to 24 hours (24 to 1 download attempts a day). When a patient's monitor 5 is ready to download in a particular bin, the time within the bin is randomly selected.

When software updates are available for the monitor 5, for example, at the remote server 204, the software updates can be received by the update manager 51 from the remote server 204 via the internal Wi-Fi modem 200 or the internal cellular data modem 202 if the monitor 5 is in the field and in use. In another example, an application provided on a mobile computing device (not shown), such as a mobile phone, laptop, or tablet computer, can be configured to allow the software update to be downloaded thereon by a patient service representative (PSR), for instance. The software download can then be transferred to the update manager 51 from the mobile computing device using either the Wi-Fi modem 202 or the cellular modem 203. The update manager 51 may not automatically install the software updates. The update manager 51 can store the software updates but delay installation thereof until the monitor 5 is brought to a maintenance facility, installation is instructed by an authorized person, or a PSR configures the monitor 5 for a new patient.

The update manager 51 can install the software update automatically in response to maintenance or configuration, or the update manager 51 can install the software update in response to an instruction from the authorized person, the service personnel, or the PSR (e.g., when the patient is instructed to visit a facility to carry out a critical update). The monitor 5 can prompt the authorized person, the service personnel, or the PSR to install the software update to the monitor 5 if a software update is available or pending, for example, by displaying an installation prompt and instructions on the display screen 43.

In an example, one processor, such as the first processor 69 (or processor core), can install the software updates, while another processor, such as second processor 71 (or processor core or a back-up processor) can continue to run the critical functions of the device. For example, such critical functions can be the ECG acquisition and analysis, and detection algorithms, as well as any of the other critical functions discussed hereinabove. In this manner, critical monitoring activities are not interrupted by a software update.

The update manager 51 or the remote server 204 can schedule installation of the software update for when the patient is at a doctor's appointment, the patient has additional protection, and/or the monitor 5 is not being used by the patient at the appointment or other alternatively monitored situation. Accordingly, if a medical event, e.g., a cardiac arrest, occurs during installation of the software update while the patient is at the doctor's office, there is no additional risk to the patient due to the monitor 5 being unavailable during the installation process. The patient can instead be serviced by an alternative or replacement device provided by the doctor or hospital during their visit. In another example, the update manager 51 can notify the remote server 204 before and after it starts the software update. Therefore, if the update is not completed within an expected time period (e.g., 5 minutes), an authorized person, the service personnel, or a PSR are automatically notified by the remote server such that the authorized person, the service personnel, or the PSR can send an alternative or replacement device to the patient. The expected time period can be set in the system as a user configurable parameter or automatically set by system based on system capacity and speed. The update manager 51 and, by association, the monitor 5 can thus be configured to avoid disruption of service to the patient due to the installation of software updates.

Alternatively, the monitor 5 can prompt the patient to install a software update. The update manager 51 receives the software updates from the remote server 204 via the Wi-Fi modem 202 or the cellular data modem 203 and stores the software updates. The monitor 5 can prompt the patient to install the software update, for example, by displaying an installation prompt and instructions on the display screen 43. The monitor 5 can prompt the patient to install the software update immediately after downloading the software update, at a predetermined time after downloading the software update, or at an assigned installation date and time.

For example, the update manager 51 can determine a time to prompt the patient to install the software update based on one or more physiological parameters of the patient that are monitored by the wearable defibrillator 1. For example, the update manager 51 can determine the time to prompt the patient to install the software update based on an ECG signal of the patient such that the prompt is provided at a time when a cardiac event is determined to be less likely to occur for the patient. The arrhythmia detection algorithms can be used to determine the time to prompt the patient to install the software update when a likelihood or probability of a cardiac event is low. In one aspect or embodiment, the time to prompt the patient to install the software update can be determined based on a medical premonitory event estimation of risk score as disclosed in U.S. Utility application Ser. No. 14/941,302, filed on Nov. 13, 2015, the entire contents of which are hereby incorporated by reference. The medical premonitory event estimation of risk score provides a likelihood or probability of a medical event, such as, a cardiac arrest, occurring for the patent. The monitor 5, in cooperation with the update manager 51, can determine the time to prompt the patient to install the software update at a time corresponding to a score that indicates that there is a low likelihood of an impending cardiac event for which operation of the wearable defibrillator 1 can be needed.

In another example, the update manager 51 can determine a time when the device is not being used, such as when the patient is not wearing the wearable defibrillator 1 or changing the battery, and run the installation procedure then. In some implementations, the update manager 51 can install a software update to one of the media storage drives while boot availability and operation of the wearable defibrillator 1 is maintained based on the other media drive. Accordingly, the update manager 51 can install the software update at any time after its download, for example, on-the-fly as the software update is received/downloaded.

In some examples, when a belt node is connected to the system, the monitor 5 can check the BNP module 17 versions for compatibility. In some examples, the monitor 5 can automatically initiate the check for compatibility in response to the BNP module 17 being connected to the monitor 5. Similarly, the monitor 5, or the update manager 51, can communicate directly with the BNP module 17 and, for example, remote server 204 to determine if one or more software updates are available for the BNP module. The version check compares two version numbers, the hardware version and the software version. In order for a given belt to work with a monitor, the hardware versions should be compatible. If the hardware versions do not match, the patient can be told that the belt is incompatible. If the hardware versions do match, the software version is checked for compatibility and, if necessary, updated to provide compatibility. For example, software versions on the BNP 17 of equal or higher value to the belt node image within the monitor 5 can be allowed to run. If the software version is less than the belt node image within the monitor 5, the belt node software can be updated according to the techniques described herein to the version of the belt node image within the monitor 5. For example, the update manager 51 can determine the time period for downloading and/or installation of the updated belt node software based on a current and/or projected operation of the BNP 17, such as, when the electrodes 7a, 7b, 7c, and 7d are not being used to treat a patient or performing some other critical function. The update manager 51 can download and install the updated belt node software to the BNP 17 at the determined time period(s). In some examples, the update manager 51 can store the data for updating the belt node software to the current belt node image within the update manager 51 in memory such that the update manager 51 does not have to download the updated belt node software before installing the updated belt node software to the BNP 17.

In some examples, the update manager 51 can control download and upload of data via the cellular modem 203 based on one or more data usage thresholds and data usage of the cellular modem 203. The update manager 51 and/or the remote server can be configured to track the data usage of the cellular modem 203 for a current period. The monitor 5 can be configured to receive software updates and other data downloads only if a data usage threshold has not been exceeded for the current period. For example, the remote server 204 can push or the update manager 51 can accept only a predetermined number of software updates or other data downloads each month based on a remaining data usage threshold for the month to avoid any overage charges by the cellular carrier. Alternatively, if an update is urgent or required, the update manager 51 can download the update even if the download results in the data usage threshold is being violated. The associated cellular data plan can be reconfigured at the end of the month or in expectation for an update in a future month to add extra data to support a software update or other data download. The update manager 51 can be configured to schedule software downloads and other updates based on the data usage and the data usage threshold such that a download is delayed or scheduled for a later period and/or a period in which a projected data usage is determined to be low, e.g., substantially below the data usage limit. The update manager 51 or the remote server can determine a projected data usage based on planned software updates and other planned or scheduled downloads for the monitor 5.

Data can be sent from the monitor 5 to the remote server 204 prior to or during a software update. For example, such data can include patient data relating to the patient associated with the medical device 1. To ensure patient privacy and data security and integrity, the data download control can perform transmission of patient data from the monitor 5 to the remote server 204 by check summing patient data using, e.g., a MD5 message digest algorithm. The check summed data can be compressed into a .tar or .gzipped format for easier transport and to ensure that the package from each monitor 5 includes a single file. The compressed data can be encrypted using, e.g., a 256-bit AES Cipher Block Chained algorithm, or another secure encryption standard used, for example, by various government agencies such as the Department of Defense (DoD). The encrypted data can be transmitted to the remote server using the UFTP application layer protocol. In this context, UFTP refers to an encrypted multicast file transfer program that uses UDP (user datagram protocol) packets, which can be adjusted to provide more reliable transmissions across lossy networks. The remote server 204 can be configured to receive the patient data. After receipt by the remote server 204, the above-described data processing stages can be performed in reverse to recover the original data.

If support personnel need to receive data from the patient/monitor 5 in the field prior to an automatically scheduled download data, a menu option under the patient menu screen can be made available to force a download to occur. The patient or operator can see the status of the download and the final result, e.g., Complete or Incomplete, with associated condition code. The status can be used by the support personnel to troubleshoot any issues that the patient can have with the download process.

Redundant Booting

Below is described an example redundant booting mechanism for use in a medical monitoring device. For illustration purposes, the example redundant booting is described in connection with the wearable defibrillator 1 above, and in the context of the system and software architecture described above. However, it is to be understood that the techniques described below can be implemented on any other medical device (including devices having different system and software architecture to that described above). Moreover, it is to be understood that the mechanism can assume various alternative orientations and, accordingly, such descriptions herein are not to be considered as limiting.

In an aspect, the monitor 5 can include one or more processors that can be configured to support redundant booting. For example, a boot loader and other software applications of the one or more processors 69, 71 can be duplicated on at least two separate media drives in case one of the drives should fail or code on a drive is corrupted. The wearable defibrillator 1 can thus boot and operate from a secondary (or third, etc.) media storage drive if a first media drive option fails or the code stored thereon is corrupted. In another example, rather than using at least two separate media drives as discussed hereinabove, a single media drive can be utilized. If a single media drive is utilized, one address line of an addressable word, such as the high address line, can be provided into/out of the circuit 76. Such a configuration can allow the circuit 76 to switch from low flash to high flash of the single media drive by setting the routed address line to either high or low.

Figure 8:
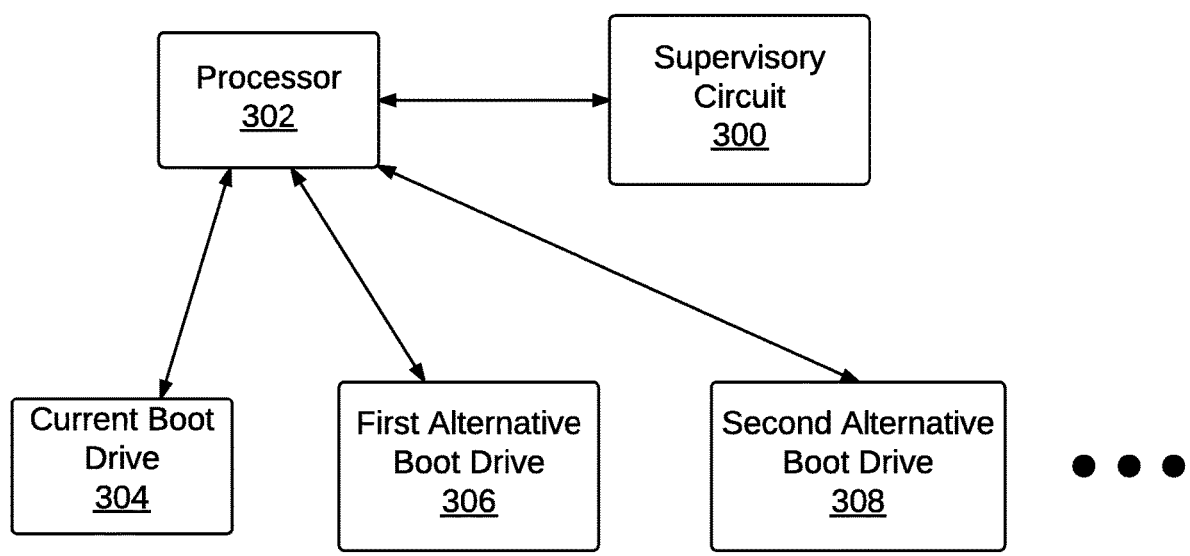
FIG. 8 is a block diagram of a redundant booting system according to an example of the present disclosure.

In some implementations, as shown in FIG. 8, the supervisory circuit 300 can be configured to monitor the booting process. If the supervisory circuit 300 detects a booting error or problem, it can cause the booting process to be re-initiated. If after a predetermined number of tries (e.g., 2-3 attempts), the booting process fails, the supervisory circuit 300 can cause a change in a boot order such that booting from another storage drive can be initiated. The number of tries can be a user configurable parameter or can be automatically set by the system. In some examples, the number of tries can be set to a default value, which can then be varied.

The supervisory circuit 300 can be configured to monitor a state of at least one processor 302 (such as BNP 17, first processor 69, and/or second processor 71), e.g., for boot errors and operation errors, when the at least one processor 302 is configured to boot from a current boot drive 304. For example, the supervisory circuit 300 can be configured to monitor a number of times that the at least one processor 302 enters a failure state during or after booting from the current boot drive 304. The supervisory circuit 30 can be configured to control the at least one processor 302 to boot from a first alternative drive 306, different from the current boot drive 304, if the processor enters the failure state a predetermined number of times. For example, the supervisory circuit 300 can control the at least one processor 302 to reboot from the current boot drive 304 the predetermined number of times in response to a boot error or an operating error of the at least one processor 302.

After the supervisory circuit 300 controls the at least one processor 302 to reboot from the current drive 304 the predetermined number of times, the supervisory circuit 300 can control the at least one processor 302 to boot from the first alternative drive 306. In some implementations, one or more alternative drives in addition to the first alternative 306 drive can be provided. For example, as shown in FIG. 8, a second alternative drive 308 can be provided, and in such an implementation, the first alternative drive 306 can become the new current boot drive after the predetermined number of reboots of the current boot drive 304, and the redundant booting mechanism can, after rebooting the new current boot drive 306 another predetermined number of times, control the at least one processor to boot from the second alternative drive 308.

Returning to FIG. 5, the supervisory circuit 300 can be implemented using a watchdog timer (WDT) scheme as described below. For example, a processor in the monitor 5 can be released from reset when power is applied to the system and must initiate the Shell module within an initial system watchdog time, e.g., within 41 seconds. The monitor 5 can include a hardware watchdog timer (WDT) 75a, 75b implemented to protect against the possibility of software lockup. The WDT 75a, 75b can comprise a single WDT, in the event of a single processor in the device, or multiple WDTs in the event of multiple processors in the device. In one example, the WDT or WDTs can be provided by the circuit 76 as WDT 75a and WDT 75b. Although aspects and embodiments are described with respect to two WDTs, the WDT design can be such that if any of the two WDTs time out, the system can reset to prevent against the possibility of race conditions between the resetting of the processors controlled by the two WDTs.

For example, a first processor (such as first processor 69) in the monitor 5 can periodically refresh its corresponding WDT 75a during system operation. If a timeout of the WDT 75a occurs, e.g., a two second timeout period, the first processor can reset and enter a safe mode that puts hardware, e.g., the converter/defibrillator hardware, into known safe states. In some examples, a processor in the monitor 5 can perform as a watchdog for the BNP 17. In this arrangement, for example, the processor can cause the BNP 17 to be restarted after, e.g., one second of non-response.

In some examples, a WDT can have two or more timeout periods. For example, a WDT can have a first timeout period corresponding to system boot, e.g., 41 seconds, and a second, different timeout period corresponding to normal monitoring, e.g., five seconds.

In an implementation, a boot order can control an order of the devices from which the processor attempts to load a startup sequence, e.g., the boot loader, the OS kernel, and/or user space. The boot order is configured for the processor by setting certain IO pins to either a logic 1 (high) or logic 0 (low). For example, if there are two boot IO pins, the processor typically has four possible boot orders, i.e., (00, 01, 10, 11), such that four different media drives can be used in the alternate to boot the system.

An example processor utilized in the monitor 5 can be a 32 bit Advanced Risc Machine (ARM Cortex core) processor. For example, such a processor can include a plurality, e.g., 5, boot selection pins, which can be configured, for example, in the following manner:

Alternate SYS_BOOT[4:0]=01111 NAND, USB, UART, MMC1;

Default: SYS_BOOT[4:0]=00110 MMC1, USB.

The SYS_BOOT 0-4 IO pins (five total pins) provide multiple boot combinations (two of which are listed above as examples).

The boot order of the processor can be typically configured by hardwiring the boot IO pins to either a logic 1 (high) or a logic 0 (low). For example, for the hardwired configuration Alternate SYS_BOOT[4:0]=01111 NAND, USB, UART, MMC1, the processor checks the NAND memory first to see if there is executable code present. If there is executable code present on the NAND memory, the processor executes the code (even if a corruption exists in the code). If there is no executable code on the NAND, the processor next checks the USB to see if there is executable code present. This process continues through boot order by following the USB check with a check of the UART, and the UART check with a check of the MMC1 until executable code is found on one of the devices.

For example, a portion of the processor 10 pins can be hardwired and one or more of the IO pins are routed into the circuit 76. For example, for the ARM processor noted above, IO pins SYS_BOOT [1:4] are hard wired and IO pin SYS_BOOT[0] is routed into the circuit 76 so the SYS_BOOT configuration is 0111X, where X is controlled by the circuit 76. The circuit 76 sets X to 1 by default to configure the system to first boot off the NAND.

The circuit 76 can be configured to perform the WDT 75a, 75b for the system as described above with respect to FIG. 5 and controls the IO pin SYS_BOOT[0] based on feedback from the WDT 75a, 75b. The software application of the wearable defibrillator 1 performs multiple checks and diagnostics on the health of the overall system. If a part of the system code is determined to be corrupted or a physical error occurs in the system memory, the software application can stop communicating with the WDT 75a, 75b in the circuit 76. Examples of the diagnostics that can be performed include the generation of MD5s for critical system files, which are checked by the system. In addition, commands between processors and, in some cases, different code objects/libraries can have timeouts. If such timeouts are exceeded, the system assumes that a component is "locked up". For example, if the system plays an audio clip but the clip never returns done (i.e., hardware or software lock-up), then a fault is detected and the system resets. Another example, is if a command is sent to the BNP 17, for instance, and a predetermined time elapses before a reply is provided by the BNP 17, then the system resets. Further diagnostics can occur if a file or library becomes corrupted. For example, if a system file/library is corrupted, then a segmentation fault can occur when that library is accessed. Finally, any local databases on the monitor 5 used by the system can have integrity checks performed on them. In response to this termination of communication, the circuit 76 can reboot the system in an attempt to recover the system from the error and return the system to a known good state. In some examples, where if the corruption or error is a one-off or one-time glitch, a reboot of the system to restore to a known good state can resolve the issue. In some cases, if there is, e.g., true code corruption or a damaged memory that cannot be cured by a reboot, the reset cycle can continue to occur.

For example, if the circuit 76 resets the system Y (e.g., 3-4) number of times because of a WDT event, the circuit 76, after the $Y^{th}$ reset, can set the IO pin SYS_BOOT[0] to 0 (low), i.e., the opposite of the default 1 (high), which causes the processor to first attempt to boot from a next device identified by the boot configuration sequence, e.g., the USB in the above example configuration. That is, the processor can skip attempting to boot from the NAND.

In some examples, the circuit 76 can comprise a hardware counter configured to increment each time the circuit 76 resets the system because of a WDT event. Accordingly, the monitor 5 including the circuit 76 does not need to rely on any software to switch the boot drive in the case of corrupted code or damaged non-volatile memory. If the boot loader, kernel, OS or other application on the first boot drive option is corrupt, the system can still switch boot drives because the secondary boot media drive contains a back-up of the code for each of these functions/modules.

The monitor 5 can automatically notify the remote server of a determined corruption or error in the system and/or notify the remote server if the circuit 76 resets the system the Y number of times, which can indicate a corrupted drive. The monitor 5 can include statistics or data on attempted execution from the drive including diagnostics on the drive and/or the code thereon.

For example, the system can attempt to copy the code image from the next device identified by the boot configuration sequence, e.g., the USB in the above example configuration, onto the first device which is determined to be corrupted or have a physical error, e.g., the NAND in the above example configuration, to recover the first device and maintain a redundant boot system. For example, after the system properly boots from an alternative drive, the processor can copy the code image from the alternative drive to any drives that have been determined as corrupted, e.g., any drives for which the circuit 76 reset the system the Y number of times during attempted booting. The circuit 76 can reset X to the default 1 (high) such that the IO pin SYS_BOOT[0] is again configured to attempt to first boot from the NAND in the above example configuration.

Although the subject matter contained herein has been described in detail for the purpose of illustration, it is to be understood that such detail is solely for that purpose and that the present disclosure is not limited to the disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

Other examples are within the scope and spirit of the description and claims. Additionally, certain functions described above can be implemented using software, hardware, firmware, hardwiring, or combinations of any of these. Features implementing functions can also be physically located at various positions, including being distributed such that portions of functions are implemented at different physical locations.

What is claimed is:

1. A wearable medical monitoring device, comprising:
   a plurality of ECG electrodes configured to receive an ECG signal of a patient when the wearable medical monitoring device is worn by the patient; and
   a monitor coupled to the plurality of ECG electrodes, the monitor configured to detect an impending cardiac event based on the received ECG signal of the patient;
   at least one processor disposed in the monitor, the at least one processor configured to execute a plurality of instructions to implement an update manager wherein the update manager is configured to
   receive a software update corresponding to the at least one software module for the monitor,
   determine an event estimation of risk score for a predetermined period of time;
   cause an installation of the software update during the predetermined period of time when the event estimation of risk score indicates a low likelihood of an impending cardiac event during the predetermined period of time; and
   cause a delay in the installation of the software update during the predetermined period of time where the event estimation of risk score indicates a high likelihood of impending cardiac event during the predetermined period of time.

2. The wearable medical monitoring device of claim 1, wherein the at least one processor comprises:
a first core and a second core, wherein the first core of the at least one processor is configured to install the software update, and wherein the second core of the at least one processor is configured to monitor the ECG signal of the patient independent of the first core.

3. The wearable medical monitoring device of claim 1, further comprising a medical treatment device configured to deliver a medical treatment to the patient wherein the medical treatment comprises a therapeutic shock.

4. The wearable medical monitoring device of claim 3, wherein the at least one processor is configured to delay installing the software update when the medical treatment device is delivering the therapeutic shock to the patient.

5. The wearable medical monitoring device of claim 1, wherein one of the at least one processor and a remote server from which the software update is made available is configured to determine if the software update affects a critical function of the monitor, and wherein the one of the at least one processor and the remote server is configured to delay the installation of the software update based on a determination that the software update affects the critical function of the monitor.

6. The wearable medical monitoring device of claim 1, wherein one of the at least one processor and a remote server from which the software update is made available is configured to determine if the software update affects a critical function of the monitor, and wherein the one of the at least one processor and the remote server is configured to delay the installation of the software update, cancel indefinitely the software update, or only partially carry out the software update based on a determination that the software update affects the critical function of the monitor.

7. The wearable medical monitoring device of claim 1, wherein the at least one processor is configured to cause a delay in the installation of the software update based on a determination of the software update affecting a function for at least one of delivering a therapeutic pulse, charging one or more capacitors, providing an alert to the patient, addressing a patient-related event detected by the device, addressing a device-related event detected by the device, and deploying conductive gel on skin of the patient.

8. The wearable medical monitoring device of claim 1, wherein the at least one processor is configured to cause a delay in the installation of the software update based on the software update affecting a function for one or more of the following: determining a treatment for the patient, preparing the treatment for the patient, and applying the treatment to the patient.

9. The wearable medical monitoring device of claim 1, wherein the at least one processor is configured to cause a delay in the installation of the software update based on the software update affecting a function for one or more of the following: determining a current or future medical event for the patient, preparing the current or future medical event for the patient, and notifying the patient and/or another party of the current or future medical event for the patient.

10. The wearable medical monitoring device of claim 1, wherein the at least one processor is configured to cause a delay in the installation of the software update based on the software update affecting a function for one or more of the following: a time needed for download, unpacking, and installation of the software update, a size of the software update, and a relationship of a type of the software update to a function of the device currently in use or scheduled for future use.

11. The wearable medical monitoring device of claim 1, wherein the at least one processor is further configured to automatically install the software update in response to a maintenance operation performed on the wearable medical monitoring device, the wearable medical monitoring device being assigned to a new patient, or an instruction from an authorized user.

12. The wearable medical monitoring device of claim 1, wherein the monitor is configured to provide a prompt to the patient or an authorized user to install the software update.

13. The wearable medical monitoring device of claim 1, wherein the software update is associated with updating at least one of the following functionalities of the wearable medical monitoring device: monitoring the ECG signal of the patient, providing defibrillation, conducting device-administered tests, receiving data from a remote server, and transmitting data to a remote server.

14. The wearable medical monitoring device of claim 13, wherein the software update is associated with monitoring the ECG signal of the patient, and wherein the software update changes a heart rate threshold associated with the functionality of monitoring the ECG signal of the patient.

15. The wearable medical monitoring device of claim 13, wherein the software update is associated with providing defibrillation, and wherein the software update changes an energy level associated with the functionality of providing defibrillation.

16. The wearable medical monitoring device of claim 13, wherein the software update is associated with conducting device-guided training modules, and wherein the software update changes a time at which the device-guided training modules are conducted.

* * * * *